United States Patent [19]

Edwards et al.

[11] Patent Number: 5,763,681
[45] Date of Patent: Jun. 9, 1998

[54] SYNTHESIS OF STABLE, WATER-SOLUBLE CHEMILUMINESCENT 1,2-DIOXETANES AND INTERMEDIATES THEREFOR

[75] Inventors: Brooks Edwards, Cambridge; Rhou-Rong Juo, Alston, both of Mass.

[73] Assignee: Tropix, Inc., Bedford, Mass.

[21] Appl. No.: 86,702

[22] Filed: Jul. 2, 1993

Related U.S. Application Data

[63] Continuation of Ser. No. 402,847, Sep. 6, 1989, abandoned, and a division of Ser. No. 680,783, Apr. 3, 1991, Pat. No. 5,225,584.

[51] Int. Cl.$^6$ .......................... C07C 43/03; C07C 69/00
[52] U.S. Cl. .......................... 568/660; 568/661; 568/633; 568/632; 560/130
[58] Field of Search .............................. 560/140, 130; 568/732, 808, 660, 661, 632, 633

[56] References Cited

U.S. PATENT DOCUMENTS

| | | | |
|---|---|---|---|
| 4,366,154 | 12/1982 | Tomesch | 424/247 |
| 4,956,477 | 9/1990 | Bronstein et al. | 549/221 |
| 4,962,192 | 10/1990 | Schaap | 536/18.1 |

FOREIGN PATENT DOCUMENTS

| | | |
|---|---|---|
| 0 254 051 | 1/1988 | European Pat. Off. |
| WO 88/00695 | 1/1988 | WIPO . |
| WO 89/06226 | 7/1989 | WIPO . |

OTHER PUBLICATIONS

A.E. Arbusow et al., *Chem. Ber.*, 60, pp. 291-295 (1927).
M. Bhatt et al., *Synthesis*, pp. 249-282 (1983).
Boutagy et al., *Chemical Reviews*, 74, pp. 87-99 (1974).
Burkhouse et al., *Synthesis*, pp. 330-332 (1984).
Creary et al., *The Journal of Organic Chemistry*, pp. 2165-2170 (1985).
Feutrill et al., *Tetrahedron Letters*, 16, pp. 1327-1328 (1970).
Feutrill et al., *Aust. J. Chem.*, 25, pp. 1731-1735 (1972).
T.W. Greene, "Protective Groups in Organic Synthesis", pp. 88-92 (1981).
Grell et al., *Chemical Abstract*, 66, pp. 53-67 (1966).
Gushurst et al., *The Journal of Organic Chemistry*, 53:15, pp. 3397-3408 (1988).
Horner et al., *Chem. Ber.*, 95:581 (1962).
Kim et al., *Synthetic Communications*, 16(8), pp. 859-863 (1986).
King et al., *Biochemical Journal*, 33, pp. 1182-1184 (1939).
Magnus et al., *Organometallics*, 1, pp. 553-559 (1982).
McMurry et al., *The Journal of Organic Chemistry*, 43:17, pp. 3255-3266 (1978).
Meijer et al., *Tetrahedron Letters*, 41, pp. 3997-4000 (1979).
Schaumann et al., *Liebigs. Ann. Chem.*, pp. 88-100 (1977).
Shah et al. *Carbohydrate Research*, 74, pp. 105-116 (1979).
Slotin et al., *Synthesis*, pp. 737-751 (1977).
Thuong et al., *Bulletin of the Chemical Society of France*, 9-10, pp. 2083-2088 (1975).
Thuong et al., *Bulletin of the Chemical Society of France*, 3-4, pp. 667-671 (1974).
Wadsworth et al., *The Journal of American Chemical Society*, 83, pp. 1733-1738 (1961).
Walker et al., *Organophos. Reags. in Org. Synth.*, pp. 155-205 (1978).
Grell et al., *Chemical Abstract*, 66:53 (1966) 76092q.
Burkhouse et al., *Chemical Abstract*, 101 (1989) 171344q.
Kim et al., *Chemical Abstract*, 107 (1985) 39936a.
Livantsov et al., *Chemical Abstract*, 105, (1986) 191247s.
Tomioka et al., *Chemical Abstract*, 111 (1989) 194888z.

*Primary Examiner*—Amelia Owens
*Attorney, Agent, or Firm*—David G. Conlin; Linda M. Buckley

[57] ABSTRACT

A novel synthesis of compound having the formula:

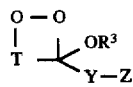

wherein T is a stabilizing spiro-linked polycycloalkylidene group, $R^3$ is a $C_1$-$C_{20}$ alkyl, aralkyl or heteroatom containing group, Y is an aromatic fluorescent chromophore, and Z is a cleavable group which, when cleaved, induces decomposition of the dioxetane ring and emission of optically detectable light, is disclosed. A tertiary phosphorous acid alkyl ester of the formula:

$$(R^1O)_3P$$

wherein $R^1$ is a lower alkyl group, is reacted with an aryl dialkyl acetal produced by reacting a corresponding aryl aldehyde with an alcohol of the formula:

$$R^3OH$$

wherein $R^3$ is as defined above, to produce a 1-alkoxy-1-aryl-methane phosphonate ester of the formula:

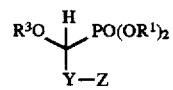

reacting the phosphonate with base to produce a phosphonate-stabilized carbanion, reacting the carbanion with a ketone of the formula:

$$T=O$$

wherein T is as defined above, to produce an enol ether of the formula:

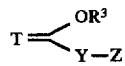

then oxygenating the double bond in the enol ether to give the corresponding 1,2-dioxetane compound.

6 Claims, No Drawings

SYNTHESIS OF STABLE, WATER-SOLUBLE CHEMILUMINESCENT 1,2-DIOXETANES AND INTERMEDIATES THEREFOR

This application is a continuation of U.S. patent application Ser. No. 07/402,847, filed Sep. 6, 1989, now abandoned. This application is a divisional of Ser. No. 07/680,783, filed on Apr. 3, 1991, now U.S. Pat. No. 5,225,584, issued Jul. 6, 1993.

BACKGROUND OF THE INVENTION

1. Field of the Invention

This invention relates to a novel chemical synthesis of stable, water-soluble chemiluminescent 1,2-dioxetanes and to novel intermediates obtained in the course of synthesizing such 1,2-dioxetanes.

2. Description of Related Art 1,2-Dioxetanes, cyclic organic peroxides whose central structure is a four-membered ring containing pairs of contiguous carbon and oxygen atoms (the latter forming a peroxide linkage), are a known, but until recently seldom utilized, class of compounds. Some 1,2-dioxetanes can be made to exhibit chemiluminescent decomposition, e.g., by the action of enzymes, as described in the following copending, commonly-assigned U.S. patent applications: Bronstein, Ser. No. 889,823,"Method of Detecting a Substance Using Enzymatically-Induced Decomposition of Dioxetanes", filed Jul. 24, 1986; Bronstein et al., Ser. No. 140,035, "Dioxetanes for Use in Assays", filed Dec. 31, 1987; Edwards, Ser. No. 140,197, "Synthesis of 1,2-Dioxetanes and Intermediates Therefor", filed Dec. 31, 1987; Edwards, et al., Ser. No. 213,672, "Novel Chemiluminescent Fused Polycyclic Ring-Containing 1,2-dioxetanes and Assays in Which They Are Used", filed Jun. 30, 1988; as well as in Bronstein, I. Y. et al., "Novel Enzyme Substrates and Their Application in Immunoassay", *J. Biolum. Chem.*, 2:186 (1968).

The amount of light emitted during such chemiluminescence is a measure of the concentration of a luminescent substance which, in turn, is a measure of the concentration of its precursor 1,2-dioxetane. Thus, by measuring the intensity of luminescence, the concentration of the 1,2-dioxetane, and hence the concentration of a substance being assayed (e.g., a biological species bound to the 1,2-dioxetane member of a specific binding pair in a bioassay) can be determined. The appropriate choice of substituents on the 1,2-dioxetane ring allows, inter alia, for adjustment of the chemical stability of the molecule which, in turn, affords a means of controlling the onset of chemiluminescence, thereby enhancing the usefulness of such chemiluminescence for practical purposes, e.g., immunoassays, nucleic acid probe assays, enzyme assays, and the like.

The preparation of 1,2-dioxetanes by photo-oxidation of olefinic double bonds is known. Mazur, S. et al., *J. Am. Chem. Soc.*, 92:3225 (1970). However a need exists for a facile, general synthesis of substituted 1,2-dioxetanes from olefinically-unsaturated precursors derived from readily available or obtainable starting materials through tractable intermediates. In this connection, a particular need exists for a commercially useful method for producing 1,2-dioxetanes of the general formula:

wherein T, R³, Y and Z are defined herein below, from enol ether-type precursors of the general formula:

McMurry et al. [McMurry, J. E., et al., *J. Org. Chem.*, 43:3255 (1978)] described titanium-induced reductive coupling of carbonyl groups to form olefins. Schaap, A. P., EPO 254,051, published Jan. 27, 1988, and Bronstein, I. Y., 1986, disclose the use of this reaction to produce compounds of formula (II) by the following general reaction:

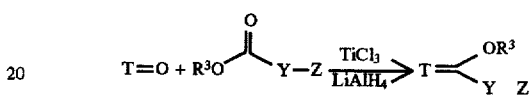

Several problems with aforementioned unsymmetrical McMurry coupling are especially important in the radical based mechanism which operates in the above equation when compared with similar mixed couplings between aliphatic and diaryl ketones where the mechanism is ionic in nature. The need to often use molar excesses of the expensive T=O ketone over ester co-reactants in an attempt to favor the mixed coupling product, while at the same time obtaining low yields at best, makes this approach suitable only for small scale preparations. Furthermore, the well-known capricious nature of the reaction, the large amounts of TiCl₃/LiAlH₄ required to effect the coupling, and the formation of by-products which are difficult to separate from the desired enol ethers also limit the commercial utility of the process. In addition, certain useful meta-substituted starting materials such as:

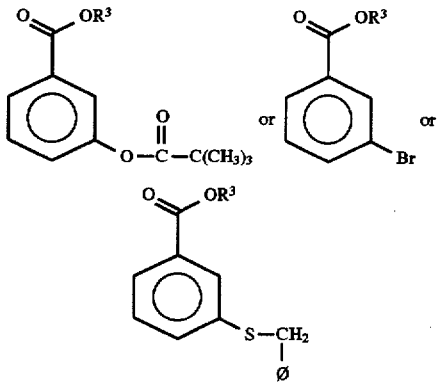

cannot be used with the McMurry reagents as such substituent groups would be reduced, hydrolysed, or would take part in reductive coupling with T=O. Thus, the double bond cannot be introduced regiospecifically in every case.

Enol ethers have also been prepared by Peterson or Wittig reactions of alkoxymethylenesilanes or phosphoranes with aldehydes or ketones in basic media [Magnus, P., et al., *Organometallics*, 1:553 (1982); Wynberg, H. and Meijer, E. W., *Tetrahedron Lett.*, 41:3997 (1979)]. Bronstein, 1986, above, describes the synthesis of an olefin of formula (II) above using a Wittig reaction of a phosphonium ylide with a T=O ketone. A major advantage of the Wittig reaction is that it is an ionic reaction, where the double bond can be introduced regiospecifically in almost every case.

One problem with the Wittig reaction, however, is that the product alkene is difficult to separate from the phosphine oxide by-product because of the similar solubility characteristics of these compounds. Another problem is that the initially-produced phosphonium ylides can be made only from relatively expensive phosphine starting materials [Walker, B. J., in Cadogan, J.I.G., ed., "*Organophosphorus Reagents in Organic Synthesis*", Academic Press, N.Y. (1978), pp. 155–205]. Also, as phosphonium ylides are relatively weakly nucleophilic, they will react only with a limited range of carbonyl compounds, and can require relatively harsh reaction conditions to do this [Gushurst, A. J., et al., *J. Org. Chem.*, 53:3397 (1988)]. Finally, side reactions frequently occur in the Wittig reactions, which also contribute to relatively low yields [Horner, L., et al., *Chem. Ber.*, 95:581 (1962)].

Because of the many problems attendant upon both the McMurry and Wittig reactions, particularly when used to synthesize olefinic intermediates for enzyme-cleavable 1,2-dioxetanes on a commercial scale, a more-suitable route to enol ether derivatives useful in the synthesis of stable, water-soluble, enzyme-cleavable chemiluminescent 1,2-dioxetanes was needed.

SUMMARY OF THE INVENTION

This invention fills this need. A new synthesis of stable, water-soluble chemiluminescent 1,2-dioxetanes, particularly ones that are enzyme-cleavable, substituted with stabilizing and solubilizing groups and ring-containing fluorophore moieties, that avoids problems inherent in previously-employed reactions, has now been discovered. In particular, this invention is concerned with a synthetic route to such 1,2-dioxetanes that employs, for the first time, dialkyl 1-alkoxy-1-arylmethane phosphonate-stabilized carbanion intermediates in the synthesis of key enol ether intermediates for the desired 1,2-dioxetane end products.

The use of phosphonate-stabilized carbanions in a Horner-Emmons reaction [Horner, L., et al., *Chem. Ber.*, 91:61 (1958); Wadsworth, W. S., *J. Am. Chem. Soc.*, 83:1733 (1961)] for the production of enol ethers used in the synthesis of stable, water-soluble, chemiluminescent 1,2-dioxetanes such as those of formula (I) above, has been found to exhibit several advantages over previous methods for synthesizing such enol ether intermediates. These include: regiospecific introduction of the olefinic double bond in the presence of a wide range of ancillary functional groups; increased nucleophilicity compared to the phosphonium ylides, which not only increases the variety of ketones with which the phosphonate-stabilized carbanions can react, but also permits this reaction to be carried out under milder conditions; more-readily separable alkene and phosphorous-containing by-products than can be obtained using the Wittig reaction (the phosphoric acid diester salt by-products produced by practicing this invention are highly water-soluble); facile betaine formation due to enhanced reactivity and stability of the phosphonate carbanions compared to the phosphonium ylides; and starting materials, i.e., trialkylphosphites, that are more cheaply and conveniently prepared than the more-expensive phosphines necessary for the Wittig reaction.

It has also been discovered that, not only does the reaction of an arylaldehyde dialkyl acetal with a trialkylphosphite or a trialkylsilyldialkylphosphite in the presence of a Lewis acid [Burkhouse, D. et al., *Synthesis*, 330 (1984); Oh, D. Y., et al., *Syn. Comm.*, 16(8):859 (1986)] provide a general and facile route to the phosphonate intermediates for Horner-Emmons reactions with T=O ketones or diones (O=T=O) than does the previously known route employing the Arbuzov reaction [Arbuzov, A. E., et al., *Chem. Ber.*, 60:291 (1927)] between an alpha alkoxy arylmethyl halide and a trialkylphosphite, but also that the aryl moiety of the thus-employed arylaldehyde dialkyl acetal, which may be open chain or cyclic (e.g., a 1,3-dioxolane or dioxane), can be substituted with electron-donating or -withdrawing meta-substituents. The resulting meta-substituted dialkyl 1-alkoxy-1-arylmethane phosphonates, with one exception not useful in the present invention [Creary, X., et al., *J. Org. Chem.*, 50:2165 (1985)], are unknown in the prior art. Meta-substituted aryl groups are preferred, as the ultimate production of an electron-donating moiety in this position, relative to the point of attachment of a 1,2-dioxetane group, has been found to maximize the efficiencies for production of singlet excited states from 1,2-dioxetanes such as those of formula (I) above, substituted at the 4-position of the dioxetane ring with a monocyclic or polycyclic aromatic ring-containing, fluorophore-forming group.

And, as disclosed and claimed in copending Edwards, et al., U.S. patent application Ser. No. 213,672, when fused polycyclic aromatic ring-containing, substituted dialkyl 1-alkoxy-1-arylmethane phosphonates are used, and the labile substituent, or its precursor, is attached to the ring at a position so that the total number of ring atoms, e.g., ring carbon atoms, including the carbon atoms at the points of attachment of the methane phosphonate group and said labile substituent, is an odd whole number, preferably 5 or greater, chemiluminescent 1,2-dioxetanes so produced, when decomposed in an appropriate environment, emit red-shifted light of greater intensity and longer duration than when the rings are otherwise substituted.

Other substituents can be included anywhere on the aromatic ring of these phosphonates, but at least one substituent which can be elaborated to a chemically or enzymatically cleavable moiety preferably is present in a meta, or odd position relative to a "benzylic" carbon atom which is further substituted by an alkoxy, aralkoxy, or an aryloxy group and the phosphorous atom of the phosphonate ester group.

An example of an elaboratable group is the bromine atom in diethyl 1-methoxy-1-(3-bromophenyl)methanephosphonate, which upon Horner-Emmons reaction with a T=O ketone yields an enol ether, e.g.:

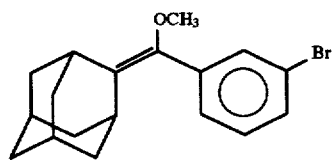

This enol ether can be converted to a Grignard reagent or an organolithium derivative for reaction with elemental sulfur, dimethyl disulfide, or methyl methylthiosulfoxide to furnish the corresponding enol ether thiophenol or its methyl ether. The same organometallic species can be reacted with trimethylsilyl azide or azidomethyl phenyl sulfide [Tanaka, N., et al., J.C.S. *Chem. Comm.*, 1322 (1983); Trost, B., et al., *J. Am. Chem. Soc.*, 103:2483 (1981)] to give the meta aminophenyl enol ether or its N-acyl or sulfonamide derivatives.

It is thus an object of this invention to provide a facile, inexpensive, high-yield, convergent chemical synthesis of stable, water-soluble, chemically, thermally and enzymatically decomposable, chemiluminescent 1,2-dioxetanes such as those of formula (I) above, by a route that employs substituted arylaldehyde alkyl and cycloalkyl acetals and novel phosphonate derivatives capable of forming phosphonate-stabilized carbanions as intermediates in the formation of the enol ether precursors of such 1,2-dioxetane end products.

It is a further object of this invention to provide methods for synthesizing the individual substituted arylaldehyde alkyl and cycloalkyl acetals, phosphonate derivatives and enol ether intermediates employed in synthesizing chemiluminescent 1,2-dioxetanes in accordance with this invention.

It is yet another object of this invention to provide as novel compositions of matter substituted arylaldehyde alkyl and cycloalkyl acetals, phosphonate derivatives and enol ether intermediates useful in the synthesis of chemiluminescent 1,2-dioxetanes.

These and other objects of this invention, as well as a fuller understanding of the advantages thereof, can be had by reference to the following disclosure and the appended claims.

DETAILED DESCRIPTION OF THE INVENTION

The 1,2-dioxetanes, and in particular the enzymatically-cleavable dioxetanes in which T is a spiro-bonded substituent, a gem carbon of which is also the 3-carbon atom of the dioxetane ring, disclosed and claimed in the aforementioned copending Bronstein, Bronstein et al., Edwards, and Edwards et al. applications, and their thermally, chemically and electrochemically cleavable analogs, form one class of water-soluble chemiluminescent 1,2-dioxetane compounds that can be synthesized by the method of this invention. These 1,2-dioxetanes can be represented by formula (I) above, T being a stabilizing group. The most preferred stabilizing group is a fused polycycloalkylidene group bonded to the 3-carbon atom of the dioxetane ring through a spiro linkage and having two or more fused rings, each having from 3 to 12 carbon atoms, inclusive, e.g., an adamant-2-ylidene, which may additionally contain unsaturated bonds or 1,2-fused aromatic rings, or a substituted or unsubstituted alkyl group having from 1 to 12 carbon atoms, inclusive, such a s tertiary butyl or 2-cyanoethyl, or an aryl or substituted aryl group such as carboxyphenyl, or a halogen group such as chloro, or heteroatom group which can be a hydroxyl group or a substituted or unsubstituted alkoxy or aryloxy group having from 1 to 12 carbon atoms, inclusive, such as an ethoxy, hydroxyethoxy, methoxyethoxy, carboxymethoxy, or polyethyleneoxy group.

The symbol $R^3$ represents a $C_1$–$C_{20}$ unbranched or branched, substituted or unsubstituted, saturated or unsaturated alkyl group, e.g., methyl, allyl or isobutyl; a heteroaralkyl or aralkyl (including ethylenically unsaturated aralkyl) group, e.g., benzyl or vinylbenzyl; a polynuclear (fused ring) or heteropolynuclear aralkyl group which may be further substituted, e.g., naphthylmethyl or 2-benzothiazol-2-yl)ethyl; a saturated or unsaturated cycloalkyl group, e.g., cyclohexyl or cyclohexenyl; a N, O, or S heteroatom containing group, e.g, 4-hydroxybutyl, methoxyethyl, or polyalkyleneoxyalkyl; an aryl group, any of which may be fused to Y such that the emitting fragment contains a lactone ring, or an enzyme-cleavable group containing a bond cleavable by an enzyme to yield an electron-rich moiety bonded to the dioxetane ring; preferably, X is a methoxy group.

The symbol Y represents a light-emitting fluorophore-forming group capable of absorbing energy to form an excited energy state from which it emits optically detectable energy to return to its original energy state. Preferred are phenyl, biphenyl, 9,10-dihydrophenanthryl, naphthyl, anthryl, pyridyl, quinolinyl, isoquinolinyl, phenanthryl, pyrenyl, coumarinyl, carbostyryl, acridinyl, dibenzosuberyl, phthalyl or derivatives thereof.

The symbol Z represents hydrogen (in which case the dioxetane can be thermally cleaved by a rupture of the oxygen-oxygen bond), a chemically-cleavable group such as a hydroxyl group, an alkanoyloxy or aroyloxy ester group, silyloxy group, or an enzyme-cleavable group containing a bond cleavable by an enzyme to yield an electron-rich moiety bonded to the dioxetane ring, e.g., a bond which, when cleaved, yields a Y-appended oxygen anion, a sulfur anion, an amino or substituted amino group, or a nitrogen anion, and particularly an amido anion such as sulfonamido anion.

One or more of the substituents T, $R^3$ and Z can also include a substituent which enhances the water solubility of the 1,2-dioxetane, such as a carboxylic acid, e.g., a carboxy methoxy group, a sulfonic acid, e.g., an aryl sulfonic acid group, or their salts, or a quaternary amino salt group, e.g., trimethyl ammonium, with any appropriate counter ion.

When using an enzymatically-cleavable 1,2-dioxetane, cleavage can be accomplished using an enzyme such as alkaline phosphatase that will cleave a bond in, for example, a Z substituent such as a phosphate mono ester group, to produce a Y oxy-anion of lower oxidation potential that will, in turn, destabilize the dioxetane and cleave its oxygen-oxygen bond. Alternatively, catalytic antibodies may be used to cleave the Z substituent. Destabilization can also be accomplished by using an enzyme such as an oxidoreductase enzyme that will cleave the oxygen-oxygen bond directly; see the aforementioned Bronstein and Bronstein et al. applications.

Besides a phosphate ester group, Z in formula I above can be an enzyme-cleavable alkanoyloxy group, e.g., an acetate ester group, an oxacarboxylate group, or an oxaalkoxycarbonyl group, 1-phospho-2,3-diacylglyceride group, 1-thio-D-glucoside group, adenosine triphosphate analog group, adenosine diphosphate analog group, adenosine monophosphate analog group, adenosine analog group, α-D-galactoside group, β-D-galactoside group, α-D-glucoside group, β-D-glucoside group, α-D-mannoside group, β-D-mannoside group, β-D-fructofuranoside group, β-D-glucosiduronate group, an amide group, p-toluene sulfonyl-L-arginine ester group, or p-toluene sulfonyl-L-arginine amide group.

The method for producing 1,2-dioxetanes according to this invention can be illustrated in part by the following reaction sequences leading to the preparation of 1,2-dioxetanes having both an alkoxy (or aryloxy) and an aryl substituent at the 4-position in which the latter (illustrated here as an aryl Y substituent) is itself substituted by one or more $X^1$ groups, these substituents being ortho, meta, or para to each other. As will be appreciated by one skilled in the art, groups $R^2$ or $X^1$ need not be static during the reaction sequences, but may be interconverted under conditions which are compatible with structural considerations at each stage.

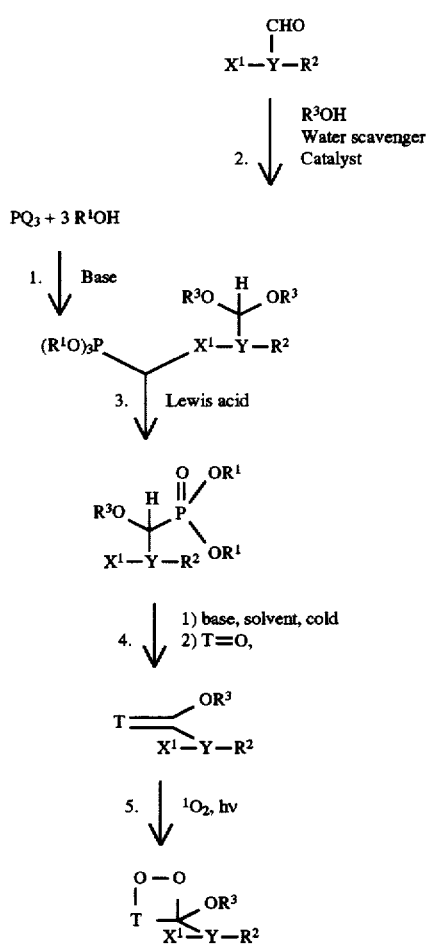

In these formulae: any Q can be independently a halogen, e.g., chlorine or bromine, or $OR^1$; $R^1$ can be independently a trialkylsilyl group or a lower alkyl group having up to 12 carbon atoms such as ethyl, propyl, or butyl; $R^2$ can be a hydroxyl group, an ether ($OR^4$) or a thioether ($SR^4$) group wherein $R^4$ is a substituted or unsubstituted alkenyl, lower alkyl or aralkyl group having up to 20 carbon atoms such as methyl, allyl, benzyl, or o-nitrobenzyl; $R^2$ can also be an acyloxy group such as acetoxy, pivaloyloxy, or mesitoyloxy, a halogen atom, e.g., chlorine or bromine, a nitro group, an amino group, a mono or di(lower) alkyl amino group or its acid salt wherein each lower alkyl substituent contains up to 7 carbon atoms such as methyl, ethyl, or butyl, where any or all of these lower alkyl groups may be bonded to Y generating one or more fused rings, a $NHSO_2R^5$ group wherein $R^5$ is methyl, tolyl, or trifluoromethyl; $R^2$ can also be a substituted aryl, heteroaryl, β-styreneyl group containing up to 20 carbon atoms such as a 4-methoxyphenyl, or 6-methoxybenzthiazol-2-yl group; $R^3$ can be a substituted or unsubstituted lower alkyl, aralkyl, or heteroaralkyl group having up to 20 carbon atoms such as methyl, trifluoroethyl, or benzyl, an aryl or heteroaryl group having up to 14 carbon atoms which may be further substituted, e.g., a 4-chlorophenyl group, a (lower) alkyl-$OSiX_3$ group wherein the lower alkyl group contains up to 6 carbon atoms such as ethyl, propyl, or hexyl and any X is independently methyl, phenyl, or t-butyl, an alkoxy (lower) alkyl group such as ethoxyethyl, or ethoxypropyl, a hydroxy (lower) alkyl group having up to 6 carbon atoms such as ethyl, butyl, or hexyl, or an amino (lower) alkyl or mono or di(lower) alkylamino alkyl group where each lower alkyl group contains up to 7 carbon atoms such as methyl, ethyl, or benzyl; $X^1$ can be hydrogen or a substituted or unsubstituted aryl, aralkyl, heteroaryl, or heteroaralkyl group having up to 20 carbon atoms such as 4,5-diphenyloxazol-2-yl, benzoxazol-2-yl, or 3,6-dimethoxy-9-hydroxyxanthen- 9-yl groups, an allyl group, a hydroxy (lower) alkyl group having up to 6 carbon atoms such as hydroxymethyl, hydroxyethyl, or hydroxypropyl, a (lower) alkyl-$OSiX_3$ group wherein the alkyl and X radicals are as defined above, an ether ($OR^4$) or a thioether ($SR^4$) wherein $R^4$ is as defined above, an $SO_2R^6$ group wherein $R^6$ is methyl, phenyl, or $NHC_6H_5$, a substituted or unsubstituted alkyl group containing up to 7 carbon atoms such as methyl, trifluoromethyl or t-butyl, a nitro group, a cyano group, an aldehydic function or its oxime or dimethylhydrazone, an alkyl halide group having up to 6 carbon atoms and the halide group being chlorine or bromine, a halogen group, a hydroxyl group, a carboxyl group or its salt, ester or hydrazide derivatives, a trisubstituted silicon-based group such as a trimethylsilyl group, or a phosphoryloxy (phosphate monoester) group.

Step 1 of the foregoing reaction sequence involves the formation of a tertiary phosphorous acid alkyl ester from a phosphorous trihalide, e.g., phosphorous trichloride or dialkylchlorophosphite, and an alcohol, e.g., a short chain alkyl alcohol, preferably one having up to 7 carbon atoms such as methanol, ethanol or butanol, in the presence of a base such as triethylamine. An alkali metal alcoholate or trialkylsilanolate can also be used in a direct reaction with the chlorophosphite.

Step 2 involves reacting an aryl aldehyde or heteroarylaldehyde with an alcohol, $R^3OH$, to give the corresponding aryl aldehyde acetal, wherein the aryl aldehyde may be a benzaldehyde, a naphthaldehyde, a anthraldehyde and the like, or aryl dialdehydes such as m- or p-phthalaldehydes and the like. The $R^2$ substituent on the aryl aldehyde, which is preferably positioned meta to the point of attachment of the aldehydic group in the benzaldehydes illustrated above, can be an oxygen-linked functional group, e.g., an ester group such as pivaloyloxy, acetoxy and the like, an ether group such as methoxy, benzyloxy, and the like, a nitro group, a halogen atom, or hydrogen (see Tables 2–6 below). Functional group $X^1$ in the aryl aldehyde may be located ortho, meta or para to the point of attachment of the aldehydic group to the aryl ring, and can be a lower alkoxy group such as methoxy, ethoxy or the like, hydrogen, or an alkyl group (see Table 2 below). In the alcohol reactant $R^3OH$, $R^3$ can be, for example, a lower alkyl group such as methyl, ethyl and the like, a lower aralkyl group, a lower alkoxy alkyl group, a substituted amino alkyl group, or a substituted siloxy alkyl group (see Tables 2–6). Diols such as ethylene glycol or propylene glycol, e.g., HO—$(CH_2)_n$—OH, produce cyclic acetals which are within the scope of this invention. The acetalization reaction between the aryl aldehyde and the alcohol or diol is carried out in conventional fashion, preferably in the presence of a catalyst such as a Lewis acid, HCl(g), p-toluenesulfonic acid or its polyvinylpyridine salt, or Amberlyst XN1010 resin, accompanied by removal of water using, e.g., trialkylorthoformate, 2,2-dialkoxypropane, anhydrous copper sulfate, or molecular sieves, or by azeotropic distillation in, for example, a Dean-Stark apparatus. In cases in which acetalization may proceed with poor conversion or yield, it is possible to use the Noyori reaction wherein any of the aforementioned alcohols ($R^3OH$) or diols are reacted with the aldehyde as their mono or bis trialkylsilyl ether with trimethylsilyl triflate as catalyst in a chlorinated hydrocarbon solvent.

Step 3 involves reacting the tertiary phosphorous acid alkyl ester (trialkylphosphite) produced in Step 1 with the aryl aldehyde dialkyl or cyclic acetal produced in Step 2, preferably in the presence of at least one equivalent of a Lewis acid catalyst such as $BF_3$ etherate or the like to give the corresponding phosphonate, essentially according to Burkhouse, D., et al., *Synthesis*, 330 (1984). Aryl aldehyde dialkyl acetals react with between 1 and 1.5 equivalents of a trialkylphosphite in the presence of a Lewis acid in an organic solvent such as methylene chloride, under an inert atmosphere, e.g., argon, at temperatures below 0° C., to produce in almost quantitative yields (see Table 2) the corresponding 1-alkoxy-1-arylmethane phosphonate esters. The phosphonates are generally oils that can be used directly or purified by chromatography on silica gel. $^1$HNMR spectra will exhibit a doublet near 4.7 ppm (J=15.5 Hz) due to the benzylic proton, split by the adjacent phosphorous Atom; occasionally, two doublets of unequal intensity will be observed.

In step 4, the phosphonate-stabilized carbanion is used to synthesize olefins by the Horner-Emmons reaction. Specifically, in Step 4.1 a phosphonate-stabilized carbanion is produced from a dialkyl 1-alkoxy-1-arylmethane phosphonate in the presence of a base such as sodium hydride, sodium amide, a lithium dialkyl amide such as lithium diisopropylamide (LDA), a metal alkoxide, or, preferably, n-butyllithium, in a suitable solvent, preferably in the presence of a slight excess of base, e.g., about 1.05 equivalents for each ionizable group present. Suitable solvents for the reaction can have an appreciable range of polarities, and include, for example, aliphatic hydrocarbons such as hexanes, aromatic hydrocarbons such as benzene, toluene and xylene, ethers such as tetrahydrofuran (THF) or glymes, alkanols such as ethanol and propanol, dimethylformamide (DMF), dimethylacetamide, and dimethylsulfoxide, and the like, or mixtures of these solvents. As lithiophosphonates are insoluble in diethylether, but soluble in ethers such as THF, reactions using LDA or n-butyllithium are preferably run in dry THF/hexane mixtures. It is also preferred to carry out the reaction in an inert atmosphere, e.g., under argon gas. At temperatures below 0° C., the reaction of n-butyllithium with phosphonates proceeds rapidly, as indicated by the instantaneous formation of a dark yellow to burgundy colored solution, depending upon the particular phosphonate used and its concentration.

In Step 4.2, the phosphate-stabilized carbanion is reacted, preferably in molar excess, with a carbonyl compound T=O or dicarbonyl compound O=T=O. When T=O is a substituted or unsubstituted adamantanone, e.g., adamantanone itself, the reaction begins immediately upon addition of the ketone, preferably from about 0.8 to about 0.95 equivalents of the ketone, to the stabilized carbanion, and goes to completion under reflux conditions in from about 2 to about 24 hours. Optimization of the T=O equivalency in each case allows complete conversion of this expensive component.

In Step 5 the enol ether is oxidized. Oxidation is preferably accomplished photochemically by treating the enol ether with singlet oxygen ($^1O_2$) wherein oxygen adds across the double bond to create the 1,2-dioxetane ring. Photochemical oxidation is preferably carried out in a halogenated solvent such as methylene chloride or the like. $^1O_2$ can be generated using a photosensitizer, such as polymer bound Rose Bengal (Hydron Labs, New Brunswick, N.J.) and methylene blue or 5, 10, 15, 20-tetraphenyl-21H.23H-porphine (TPP). Chemical methods of dioxetane formation using triethylsilylhydrotrioxide, phosphite ozonides, or triarylamine radical, cation mediated one-electron oxidation in the presence of $^3O_2$ can also be utilized.

When the oxygen-linked functional group $R_2$ on the aryl ring of the enol ether is an alkoxy group or pivaloyloxy group, it can be converted to an enzyme-cleavable group such as a phosphate, acetoxy, or O-hexopyranoside group, by carrying out the following additional steps involving the enol ether produced in Step 4 of the foregoing reaction sequence prior to carrying out the oxidation reaction of Step 5, as shown below:

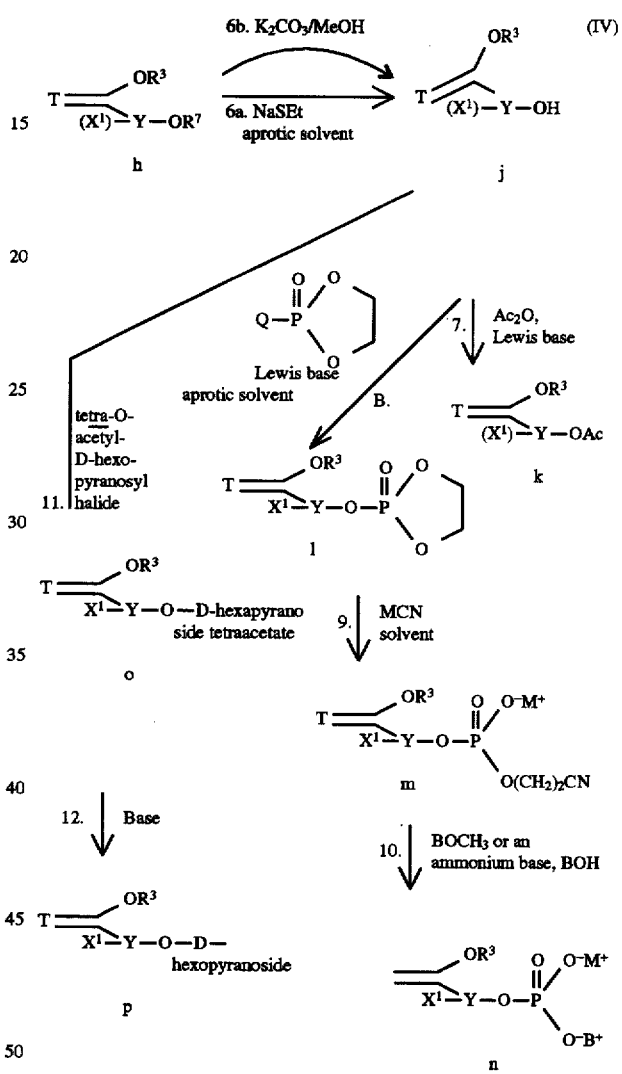

Step 6a. involves Aryl ether cleavage of the $R^7$ substituent (wherein $R^7$ is preferably methyl, allyl or benzyl), preferably with sodium thioethoxide, in an aprotic solvent such as DMF, NMP, or the like, at temperatures from about 120° C. to about 150° C. The cleavage can also be accomplished with soft nucleophiles such as lithium iodide in refluxing pyridine, sodium cyanide in refluxing DMSO, or $Na_2S$ in refluxing N-methyl-2-pyrrolidone. When $R^7$ is pivaloyl, ester cleavage can be accomplished with NaOMe, KOH or $K_2CO_3$ in an alcoholic solvent such as MeOH at temperatures from about 25° C. to reflux (Step 6b.).

The acylation of the Aryl hydroxyl group in the thus-obtained hydroxy compound is carried out in Step 7 by adding a small equivalent excess of an acid halide or anhydride, e.g., acetic anhydride, or oxalyl chloride with Lewis base, e.g., triethylamine, in an aprotic solvent.

The substituent Q on the cyclic phosphorohalidate used in Step 8 is an electronegative leaving group such as a halogen. The monovalent cation $M^+$ of the cyanide used in Step 9 can be a metallic or alkali metal cation such as $Na^+$ or $K^+$, or a quaternary ammonium cation. The cation $B^+$ of the ammonium base of Step 10 is an ammonium cation; however, NaOMe can also be used as the base. T, $R^3$ and $X^1$ are as defined above.

Steps 8, 9 and 10 can be performed separately or in a one-pot or two-pot operation. A cyclic phosphorohalidate, e.g., cyclic phosphorochloridate, is preferred for use in Step 8 not only because of its monofunctionality, chemoselectivity and enol ether-compatible deprotection mode of action, but also because it is $10^6$ times more reactive than the corresponding acyclic compounds. In a 3-step, 2-pot operation, the Aryl hydroxyl group in the free hydroxyl product produced in Step 6 is reacted with 2-halo-2-oxo-1, 3,2-dioxaphospholane to yield the cyclic phosphate triester (Step 8). This triester is subjected to ring opening with MCN (e.g., NaCN) to yield the corresponding 2-cyanoethyl diester (Step 9). A base, e.g., ammonium hydroxide or NaOMe, then provokes a facile β-elimination reaction, yielding a filterable disodium sodium ammonium salt (Step 10). In benzene, THF, diethylether or DMF, phosphate triester formation induced by a Lewis base (e.g., a tertiary amine such as triethylamine) or with a preformed alkali metal salt of the phenolic enolether can be effected with phosphorohalidates over a temperature range of about $-30°$ to about $60°$ C. Subsequently, if a pure monosodium cyanoethylphosphate ester is desired, the ring cleavage with alkalicyanide (MCN) in DMF or DMSO can be carried out in a narrow temperature range of between about $15°$ and about $30°$ C. However, in a one-pot or in situ mode this is not as important, and the temperature range widens to about $60°$ C. on the high end.

Aryl phosphate disalts can also be made from the aryl alcohol enol ether product of Step 6 (formula IV) using an activated phosphate triester of the general formula:

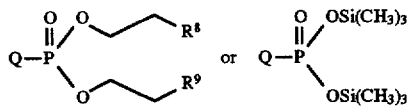

wherein Q is as described above, and $R^8$ and $R^9$ are each independently —CN, —$NO_2$, arylsulfonyl, or alkylsulfonyl. Alternatively, the phosphate triester may contain two trimethyl silyl groups, linked to the phosphorous, as shown in the formula above. This reaction can be carried out in the presence of a Lewis base in an aprotic solvent, and yields an aryl phosphate triester. The triester can then be hydrolyzed with a base, $M^+OH^-$ or $M^{+-}OCH_3$, wherein the cation $M^+$ is an alkali metal, $NR^{10}_4{}^+$ wherein $R^{10}$ is hydrogen or a $C_1$-$C_7$ alkyl, aralkyl, aryl or heterocyclic group, to give the corresponding arylphosphate monoester disalt via β-elimination. Dioxetane formation of the reaction of singlet oxygen ($^1O_2$) with these enol ether phosphate triesters, followed by similar base-induced deprotection to the dioxetane phosphate monester, may also be carried out.

An alkoxy group on the aryl ring of the enol ether can be converted to a D-sugar molecule linked to the ring via an enzyme cleavable glycosidic linkage by reacting the phenolic precursor in an aprotic organic solvent under an inert atmosphere with a base such as NaH and, with a tetra-O-acetyl-D-hexopyranosyl halide to produce the aryl-O-hexopyranoside tetraacetate (Step 11). The protective acetyl groups can then be hydrolyzed off using a base such as $NaOCH_3$, $K_2CO_3$, or $NH_3$ gas, in an alcohol such as methanol, first at $0°$ C. and then at $25°$ C. for 1 to 10 hours (Step 12), leaving a hexosidase-cleavable D-hexopyranosidyl moiety on the aryl ring.

When the enol ether aryl phosphates are oxidized to a the corresponding 1,2-dioxetanes (Step 5 above), ion exchange to a bis-quaternary ammonium or monopyridinium salt allows the facile photooxygenation of 0.06M chloroform solutions in the presence of, preferably, methylene blue or TPP, at cold temperatures, e.g., about $5°$ C. Slower reaction rates and increased photolytic damage to the product may occur with the use of solid phase sensitizers such as polymer-bound Rose Bengal (Sensitox I) or methylene blue on silica gel.

Aryl monoaldehydes or heteroaryl monoaldehydes other than those having formulas such as:

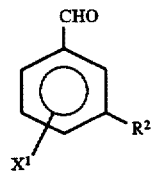

can also be used as starting materials in carrying out the above-described reaction sequences. Included among such aryl monoaldehydes are polycyclic aryl or heteroaryl monoaldehydes such as those having the formula:

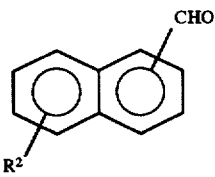

wherein $R^2$ is as defined above and is preferably positioned so that the total number of ring carbon atoms separating the ring carbon atom to which it is attached and the ring carbon atom to which the aldehyde group is attached, including the ring carbon atoms at the points of attachment, is an odd whole number, preferably 5 or greater; see Edwards, et al., U.S. patent application Ser. No. 213,672.

Fused heterocyclic acetals or hemiacetals can also be used as starting materials in carrying out the above-described reaction sequences. Included among such fused heterocyclic acetals are those having the formulae:

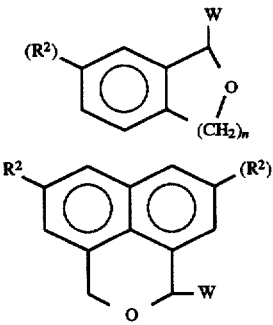

-continued

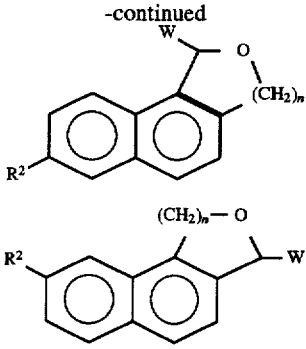

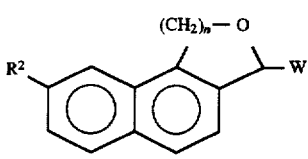

and the like, wherein $R^2$ is as described above, and nW can be $OR^3$, wherein $R^3$ is described above, or OH, and is an integer greater than zero.

Aryl or heteroaryl dialdehydes can also be used as the aldehydic starting material, e.g., ones having the formula:

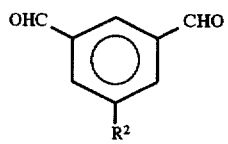

wherein $R^2$ is as described above.

Purification of the thus-obtained water-soluble dioxetanes is best achieved at alkaline pH values, e.g., about 7.5 to about 9.0, using reverse phase HPLC with an acetonitrile-water gradient, followed by lyophilization of the product, according to Edwards et al., U.S. patent application Ser. No. 244,006.

Typical enzymatically-cleavable water-soluble chemiluminescent 1,2-dioxetanes for use in bioassays which can be prepared by the method of this invention are the 3-(2'-spiroadamantane)-4-methoxy-4-(3"-phosphoryloxy)phenyl-1,2-dioxetane salts represented by the formula:

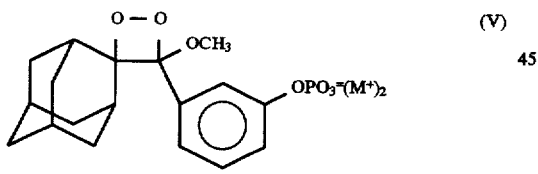

wherein $M^+$ represents a cation such as an alkali metal, e.g. sodium or potassium, or a $C_1$–$C_{18}$ alkyl, aralkyl or aromatic quaternary ammonium cation, $N(R^{10})_4^+$, in which each $R^{10}$ can be alkyl, e.g., methyl or ethyl, aralkyl, e.g., benzyl, or form part of a heterocyclic ring system, e.g., N-methylpyridinium, a fluorescent onium cation, and particularly the disodium salt. A more systematic name for the latter is 3-(4-methoxyspiro[1,2-dioxetane-3,2'-tricyclo[3.3.1.1$^{3,7}$]decan]4-yl)phenylphosphate disodium salt.

The availability of the herein described Horner-Emmons methodology and a pool of reactants containing the particular aforementioned class of mono and bis-phosphonate esters along with T=O ketones or O=T=O diones such as 2,6-adamantanedione, allows the synthesis of four different enol ether product types, one of which is a backbone condensation polymer (formula VI)

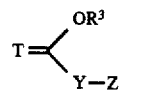

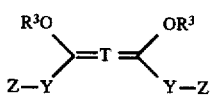

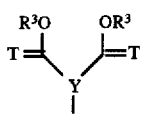

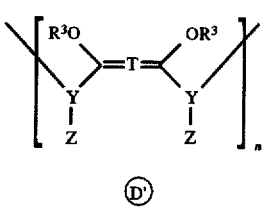

wherein T, $R^3$, Y and Z are as described herein above. These can then be converted to the corresponding 1,2-dioxetanes shown below in formula (VII) with singlet oxygen as described herein above.

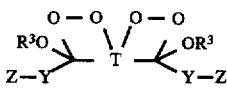

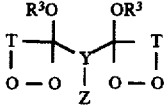

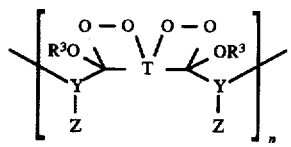

In the case of 1,2-dioxetane B of formula (VII), one T group serves to stabilize two dioxetane rings; however, each ring must be destabilized individually by chemical or enzymatic means at each Z group. In 1,2-dioxetanes C and D (polymer), one Z group can activate the decomposition of two dioxetane rings, especially if all groups appended to aromatic ring Y are disposed in a meta or odd-pattern relationship with one another as described above. If these conditions are met, then the main-chain dioxetane polymer, which may be solvent or water-soluble in these examples, will degrade to monomeric di-carbonyl units with the emission of light upon removal of the Z group to generate for example an oxy-anion at each pendant Y group in the polymer. Monomeric dioxetane C, if all-meta or odd-patterned, behaves similarly in that one event capable of splitting Z controls the fragmentation of two dioxetane rings such that more light per event can be obtained.

Schaap, 1988, above, describes the use of acids, bases, salts, enzymes, inorganic and organic catalysts, and electron donors as activating agents to remove a Z group. Labile aryl and alkyl carboxyl esters, removable with the activating agents to form aryl oxide anions (Z oxy-anions) are also disclosed; electron acceptors are not disclosed in this publication. Two ester functions classically used in chemical reactions leading to chemiluminescence, which also simultaneously release phenolate anions, are the acridinium esters (charged heteroaryl carboxyl ester), and oxalate esters (alpha-oxo-carboxyl ester) of phenols. In each case light is generated through an oxidative reaction with hydrogen peroxide (electron acceptor or oxidizing agent) and base. In the later case, however, a fluorescer must also be present as an energy acceptor in order to realize high quantum yields. Aryl oxide anions are generated as simple leaving groups in these reactions and thus are not part of the light emission process per se, nor are they utilized further. If these aromatic ring appended oxy-anions are structured so that they are preformed, chemiluminescent leaving groups, then hydrogen peroxide, whether generated in an enzymatic reaction or added from without, can function as an electron accepting activating agent which acts on alpha-oxo-carboxyl esters or N-methylacridinium-9-carboxyl esters of 1,2-dioxetanes resulting when the corresponding enol ether esters, of the type produced in Step 7 in formula (IV) above, are subsequently photooxygenated as in Step 5 in formula (III) above. These dioxetanes, illustrated generally below in formula (VIII), can produce light from both the Z group decomposition and from chemiluminescent decomposition of the leaving group simultaneously.

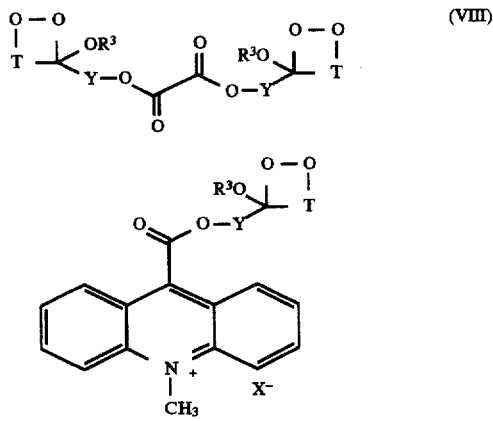

(VIII)

The acridinium ester can produce as many as two photons of light (not necessarily at the same wavelength) per molecule of hydrogen peroxide, while the oxalate ester in the presence of an acceptor may produce as many as three photons per molecule of hydrogen peroxide. The process may be optimized for aqueous or non-aqueous environments by the addition of $X^1$ groups to Y, or solubilizing groups to Y, T, or $R^3$ as defined above. It is also implicit that the same meta, or odd-pattern relationship as described above will represent the preferred positions of attachment of both the 1,2-dioxetane ring and the chemiluminescent acyloxy group to the aryl ring Y.

If the principles disclosed for bis-1,2-dioxetane C in formula (VII) above are applied here then the generalized structures shown in formula (IX) are apparent:

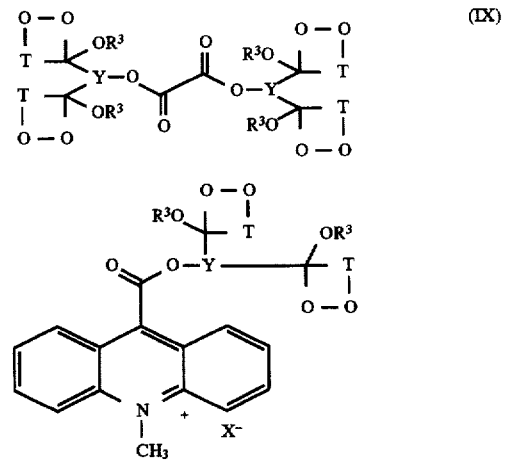

(IX)

Thus the phenol enol ether of Example 7 below can be reacted with 0.5 equivalents of oxalyl chloride in the presence of triethylamine to give the oxalate ester which exhibits a melting point of 163°–166° (formula (X)). Two ester carbonyl adsorptions are noted in the infrared spectrum at 1780 and 1755 cm$^{-1}$. Reaction with acridine-9-carbonyl chloride hydrochloride followed by N-alkylation with methyl triflate gives the acridinium ester ($X^-=OSO_2CF_3$) (formula (X)). Subsequent conversion of either compound to the corresponding bis or mono-dioxetane proceeds as indicated in Step 5 (of formula (III).

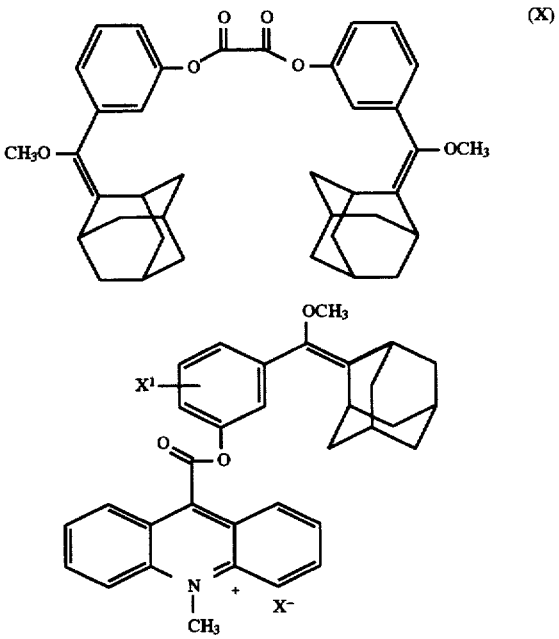

(X)

The bis-enol ether phenol of formula (XI) below is synthesized by sodium ethane thiolate cleavage of the aromatic methoxy group (Step 6 of the flow chart (III)) of the compound described in Examples 62 and 105 below. The product can be converted to any one of the enzyme cleavable groups described above, e.g., a phosphate mono ester. As such it represents a pivotal intermediate for the synthesis of 1,2-dioxetanes of type C of formula (VII) as shown above.

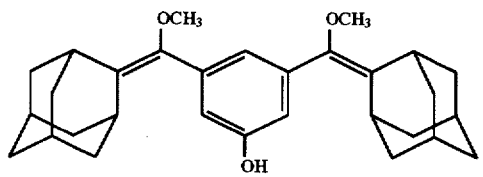

However, use of oxalyl chloride or acridine-9-carbonyl chloride-HCl gives poly enol ethers of formula (XII) below which upon conversion to the dioxetanes can, in the presence of a fluorescer such as fluorescein for the oxalate ester case, generate as many as three or five photons for every molecule of hydrogen peroxide (along with alkali, nitrogen base, or catalysts) causing removal of the chemiluminescent Z groups.

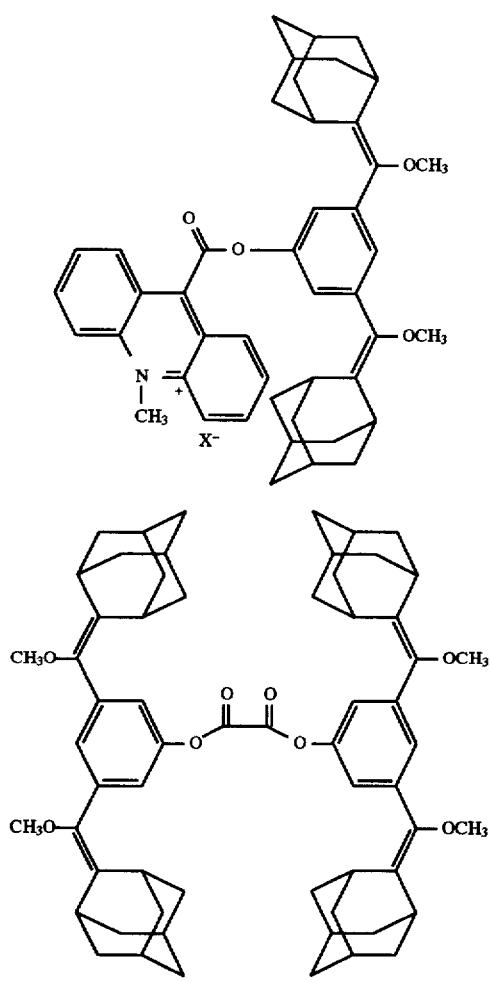

Such chemiluminescent water-soluble dioxetanes and their derivatives can be used in a variety of detection techniques, such as ligand binding assays and enzyme assays. Immunoassays and nucleic acid probe assays are examples of ligand binding techniques, in which a member of a specific binding pair is, for example, an antigen-antibody pair, or a nucleic acid target paired with a probe complementary to and capable of binding to all and or a portion of the nucleic acid. The ligand: an antibody and a nucleic acid probe, can be labeled with an enzyme and a chemiluminescent water-soluble dioxetane used as a substrate, or a chemiluminescent dioxetane can be used as a label directly and conjugated to a ligand and activated to emit light with heat, suitable chemical agents, and enzymes. Such assays include immunoassays to detect hormones, such as β-human chorionic gonadotropin (βHCG), thyroid stimulating hormone (TSH), follicle stimulating hormone (FSH), luteinizing hormone (LH) or the like, cancer markers, such as alpha fetal protein (AFP), carcinoembryonic antigen, cancer antigen CA 19-9 for pancreatic cancer, cancer antigen CA125 for ovarian cancer, haptens, such as digoxin, thyroxines prostaglandins, and enzymes such as phosphatases, esterases, kinases, galactosidases, or the like, and cell surface receptors. These assays can be performed in an array of formats, such as solution, both as a two-antibody (sandwich) assay or as a competitive assay, in solid support such as membranes (including Western blots), and on surfaces of latex beads, magnetic beads, derivatized polystyrene tubes, microtiter wells, and the like. Nucleic acid assays can be used to detect viruses e.g. Herpes Simplex Viruses, HIV or HTLV I and III, cytomegalovirus (CMV), human papiloma virus (HPV), hepatitis C core virus antigen ($HB_cV$), Hepatitis B surface antigen ($HB_sV$), Rotavirus, or bacteria, e.g., campylobacter jejuni/coli, E. coli, ETEC heat labile and stable, plasmodium falciparum, or oncogenes, or in forensic applications using human finger-printing probes, mono and multi loci. The nucleic acid detections can be performed for both DNA and RNA in a variety of formats, e.g., solution, derivatized tubes or microtiter plates, membranes (dot, slot, Southern and Northern blots) and directly in tissues and cells via in-situ hybridization. DNA and RNA can also be detected in sequencing techniques and histocompatibility assays using chemiluminescent dioxetanes. Such chemiluminescent water-soluble dioxetanes can also be used in biosensors where the ligand-binding reaction occurs on a surface of a semiconductor layer which detects chemiluminescence as photocurrent.

Furthermore, these dioxetanes can be used in in vivo applications both for diagnostics, such as imaging tumor sites when coupled to a tumor site-specific monoclonals and other ligands, or as a therapeutic, such as in photodynamic therapy to photosensitive hematoporphyrins to generate singlet oxygen—the cytotoxic agent. In addition, enol ethers—the precursors to 1,2-dioxetanes can be used as singlet oxygen scavengers both in vivo and in vitro, to monitor and/or inactivate this very reactive species.

In order that those skilled in the art can more fully understand this invention, the following examples are set forth. These examples are given solely for purposes of illustration, and should not be considered as expressing limitations unless so set forth in the appended claims.

EXAMPLE 1

5-Methoxyisophthaldehyde 3,5-Bishydroxymethylanisole was synthesized according to the procedure of V. Boekelheide and R. W. Griffin, Jr., *J. Org. Chem.*, 34, 1960 (1969). This diol (366 mg., 2.17 mmol) was added as a solid to a stirred slurry of 3 g. crushed 3 Å molecular sieves and 2.5 g. pyridinium dichromate (6.65 mmol) in 20 ml dichloromethane. After 3 hours at room temperature, the mixture was diluted with 40 ml ether and filtered through celite, and washed with 2:1 ether-dichloromethane. The orange filtrate was concentrated to a solid which was boiled with 3×30 ml hexanes, decanting the supernate each time from a gummy residue. As the combined hexane fractions cooled to room temperature, fine white needles developed in the colorless mother liquor. Filtration and drying provided 150 mg (42%) of the dialdehyde which exhibited a melting point of 110°–112° C. NMR and IR data are listed in Tables 3 and 7. TLC showed one spot (K5F, 10% ethyl acetate: dichloromethane; Rf=0.75). These data support the structure:

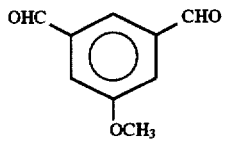

EXAMPLE 2

4-Ethoxy-3-methoxybenzaldehyde

Vanillin (10 g., 66 mmol) in acetonitrile (100 ml) was treated with finely-powdered, anhydrous potassium carbonate (12 g., 87 mmol) with vigorous stirring to yield a mobile suspension. Diethyl sulfate (11 ml, 84 mmol) was added at room temperature. The suspension was brought to reflux, becoming quite thick after 10 minutes, but thinning again after 20 minutes. Refluxing was continued for 48 hours, at which point water (5 ml) was added. After an additional 2 hours of reflux, the mixture was cooled and treated with 500 ml ice water. Stirring at 0° for several hours produced a granular precipitate which was filtered off and washed with water. Air drying afforded 11.5 g. of the product (97%) as an off-white solid melting at 61°–62.5° C. NMR and IR data are listed in Tables 3 and 7.

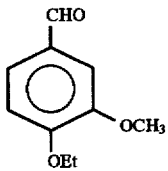

EXAMPLE 3

3-Methoxy-2-methylbenzaldehyde

This compound was synthesized according to the method of Kende, A. S., et al., *J. Am. Chem. Soc.*, 101:1860 (1979). As seen in Tables 3 and 7, NMR and IR data are identical to those reported. TLC showed the title compound to be homogeneous (K5F, 20% $CH_2CL_2$: hexanes; Rf=0.17). The major by-product in this reaction was 2-methoxybenzylphenysulfide (Rf=0.38 under the same conditions).

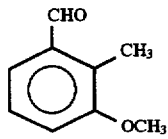

EXAMPLE 4 m-Methoxybenzaldehyde dimethyl acetal m-Anisaldehyde (204.3 g, 1.5 mol) was placed in a 1 liter flask under an argon atmosphere. Trimethyl orthoformate (191 g, 1.8 mol) was added quickly, followed by 150 ml anhydrous methanol. Amberlyst XN-1010 resin (2.1 g, Aldrich Chemical Co.), which had been previously boiled with methanol was added. The mixture was stirred at room temperature for 22 hours with the exclusion of moisture. Sodium bicarbonate (1.5 g) was added with stirring. After 20 minutes the mixture was filtered under vacuum into a 2 liter flask which was placed on the rotory evaporator with the water bath temperature at 40° C. Over 30 minutes the bath was heated to 80° to produce a clear, colorless oil. With magnetic stirring, the oil was pumped at 65° under vacuum (2 mm Hg) for 30 minutes. The resulting product weighed 272.5 g (99.8%). I.R. (neat, $cm^{-1}$): 2935, 2824, 1598, 1584, 1350, 1258, 1100, 1050, 984, 772. 1HNMR (400 MHz, $CDCl_3$): δ3.33 (6H, s, $OCH_3$); 3.81 (3H, s, $ArOCH_3$); 5.35 (1H, s, $ArCH(OCH_3)_2$; 6.87 (1H, br d, 8.1 Hz); 7.00–7.03 (2H, m); 7.27 (1H, t, 8.1 Hz). These data indicated that the product was pure enough for use in the next step and were consistent with the following structure:

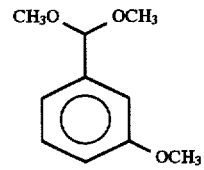

EXAMPLE 5

Diethyl 1-methoxy-1-(3-methoxyphenyl)methane phosphonate m-Methoxybenzaldehyde dimethyl acetal from Example 4 (271.4 g, 1.49 mol), triethyl phosphite (250.3 g, 1.51 mol), and methylene chloride (600 ml) were charged into a 3 liter 3-necked flask which was outfitted with a dropping funnel, an argon inlet, and an argon outlet. The flask was flushed with argon and the funnel was capped with a septum. The mixture was stirred and cooled to –40° in a liquid nitrogen-acetone bath. Boron trifluoride etherate (198.1 ml, 1.61 mol) was then added dropwise from the funnel over a 25 minute period. The mixture was allowed to slowly warm up to 5° over 3 hours. Stirring was then continued at room temperature for another 15 hours. The light yellow solution was then stirred rapidly as 500 ml saturated sodium bicarbonate solution was added. After 1 hour the mixture was transferred to a separatory funnel. The organic layer was isolated and washed with 500 ml water, 2×300 ml saturated sodium bisulfite, and 300 ml saturated bicarbonate solution. Drying was accomplished over 30 g anhydrous sodium sulfate just before decolorizing carbon (3 g) was added to the solution, and the whole was filtered under vacuum through celite. Concentration on the rotory evaporator and high vacuum pumping to a final pressure of 0.15 mm Hg at 100° C. provided a light yellow oil weighing 380 g (90%). I.R. (neat, $cm^{-1}$): 2974, 1596, 1582, 1480, 1255 (P=O ), 1098, 1050, 1020, 965. $^1$HNMR (400 MHz, $CDCl_3$): δ1.21 and 1.25 (6H, two t, 7 Hz, $OCH_2CH_3$); 3.37 (3H, s, $ArCHOCH_3$); 3.80 (3H, s, $ArOCH_3$); 3.90–4.10 (4H, m, $OCH_2CH_3$); 4.46 (1H, d, 15.6 Hz, $ArCHPO$); 6.85 (1H, m); 7.00 (2H, m), 7.26 (1H, m). This product was sufficiently pure for use in a Horner-Emmons reaction. However, further purification to remove a trace of a non-polar fluorescent impurity may be accomplished with silica gel chromatography using dichloromethane to elute the impurity and subsequent elution with 20% ethyl acetate in dichloromethane to elute the phosphonate.

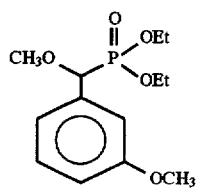

EXAMPLE 6

α-2-Adamantylidene-α-methoxy-m-methoxytoluene

One hundred grams of the phosphonate ester from Example 5 (0.347 mol) were dissolved in 650 ml HPLC grade THF (no special precautions to dry the solvent were taken). The solution was placed in a dry 2 liter, 3-necked flask which was outfitted with an addition funnel connected to an argon outlet, an argon inlet, and a septum.

After purging with argon, the flask was lowered into a dry ice/acetone bath at –78° and magnetic stirring was initiated. After stirring for 10 minutes, a solution of n-butyllithium in hexane (217 ml of a 1.6M solution, 0.347 mol) was added by syringe in several portions over 10 minutes. The resulting deep red solution was stirred at –78° for another 45 minutes. A solution of 2-adamantanone (49.47 g, 0.33 mol) in 200 ml THF was then added in a thin stream from the funnel over 5 minutes.

The cooling bath was removed and the stirred mixture was slowly allowed to warm to approximately 0° over 1.5 hours. At this point the slightly cloudy red solution was heated to reflux for 4 hours whereupon a clear, light red solution was obtained after gas evolution ceased.

During cooling to room temperature, the solution became light yellow-brown after exposure to the atmosphere. The mixture was carefully rotovapped (foaming) to remove 750 ml of the solvent. Hexane (500 ml) was added, and the resulting slurry was extracted with 500 ml water. The aqueous layer was back extracted with hexane (250 ml) and the combined organics were extracted with saturated brine (2×250 ml). The hexane solution was dried over anhydrous potassium carbonate and treated with 1 g. decolorizing carbon. Filtration through celite, followed by evaporation produced a light yellow viscous oil which was pumped at 90° with stirring under high vacuum to remove a small amount of residual adamantanone.

The final weight of the crude product was 94 g. The infrared spectrum showed no carbonyl absorption due to adamantanone (1705 cm$^{-1}$) or the corresponding adamantyl methoxyphenyl ketone (1670 cm$^{-1}$). Although this product was sufficiently pure for subsequent reaction, it was found that an identical procedure using 46.8 g. 2-adamantanone (0.9 equivalents) provided an oil, which when passed through a silica gel column (15 cm×3.5 cm) and eluting with 2% ethyl acetate in hexanes, gave an oil which solidified in the cold. Recrystallization from a minimal amount of hexanes yielded a waxy, white solid melting at 34°–37° C. Anal. Calcd for $C_{19}H_{24}O_2$: C, 80.24; H, 8.51. Found: C, 81.23; H, 8.49.

Both the crude oil and the waxy solid gave identical I.R. and NMR spectra:

I.R. (neat, cm$^{-1}$): 2900, 2838, 2655, 2640, 2620, 1655, 1600, 1592, 1580, 1574, 1444, 1282, 1240, 1202, 1095, 1078.

$^1$HNMR (400 MHz, CDCl$_3$): δ1.75–2.05 (12H, m, adamantyl); 2.66 (1H, br s, Hα$_1$); 3.27 (1H, br s, Hα$_2$); 3.31 (3H, s, OCH$_3$); 3.83 (3H, s, ArOCH$_3$); 6.82–6.94 (3H, m); 7.23–7.30 (1H, m).

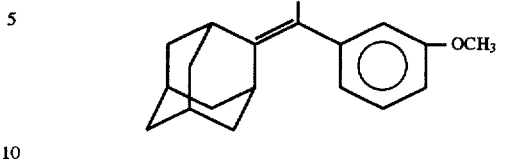

EXAMPLE 7

3-Pivaloyloxybenzaldehyde

3-Hydroxybenzaldehyde (2.04 g., 16.7 mmol) in 25 ml dichloromethane under an argon atmosphere was treated with triethylamine (3.5 ml, 25.1 mmol). The solution was cooled to 0° in an ice bath. Trimethylacetyl chloride (2.3 ml, 18.4 mmol) was added dropwise via syringe with magnetic stirring. After ten minutes, the ice bath was removed and the mixture was stirred overnight at room temperature. The reaction was quenched with 100 ml saturated sodium bicarbonate solution. The organic layer was separated and the aqueous layer extracted again with dichloromethane (2×30 ml). The combined organics were dried over anhydrous sodium sulfate and concentrated in vacuo to an orange residue which was passed through a short silica gel plug with dichloromethane as eluent.

The solvent was evaporated from the silica gel eluate to yield 3.40 g. (quant.) of the title compound as a light yellow oil which was homogeneous according to TLC (K5F, 20% ethylacetate: hexanes). See Tables 3 and 7 for NMR and IR data.

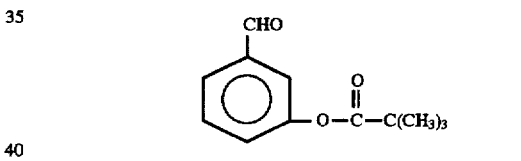

The pivaloyl ester group is not deacylated under the acidic conditions required for acetal and phosphonate synthesis which are described in Examples 4 and 5 for the 3-methoxy derivatives, but they also serve as general procedures. The resulting diethyl 1-methoxy-1-(3-pivaloyloxyphenyl) methane phosphonate is used as follows to procure methoxy (3-hydroxyphenyl)methylene adamantane.

Lithium diisopropylamide (LDA) solution was freshly prepared in the following manner. A dry, three-necked, 2 L, round bottomed flask was equipped with a magnetic stirring bar, a reflux condenser, a gas-inlet and a 500-ml dropping funnel. The flask and dropping funnel were flamed in a stream of argon. To the flask was added 78 ml (0.56 mole) of diisopropylamine and followed by 500 ml of dry THF (Baker, reagent grade). The solution was stirred and cooled to –78° in an acetone-dry ice bath, while 202 ml (0.51 mole) solution of 2.5M n-butyllithium in hexane (Aldrich) was transferred from the bottle to a dropping funnel via a double-tipped needle (3 ft., 16 gauge, Aldrich) and then added dropwise to the solution over 20 min. After another 20 min. of stirring at –78°, the 500-ml dropping funnel was rapidly replaced with a 250-ml dropping funnel containing a solution of 151.4 g (0.42 mole) of phosphonate in 120 ml THF. The addition of phosphonate to LDA solution at –78° caused a color change immediately. After addition was completed (over 15 minutes), the resulting deep red mixture was stirred at −78° for 1 hour longer. Then 49.1 g (0.33 mole) of 2-adamantanone was added. The mixture was stirred at −78° for 10 minutes and allowed to warm to room temperature in ca. 1.5 hour, and finally brought to reflux for 1.5 hour. Vigorous gas evolution was noticed during refluxing. The cooled reaction mixture was treated with 0.5 L of saturated NaHCO₃ solution for 10 minutes and poured into a 4 L separatory funnel containing 2 L of water. The aqueous phase was extracted three times with 10% EtOAc in hexane (3×250 ml). The combined organic phase was washed with 1.5 L of water, then with 1.5 L of brine and dried over Na₂SO₄. Removal of solvent gave 135.5 g of viscous brown oil. The crude product was diluted with 100 ml of 10% EtOAc in hexane and loaded onto a column (O.D.-4.5 cm., length-40 cm.), packed with 80 g of silica gel (60–200 mesh, Baker). Elution with 10 to 20% EtOAc-hexanes gave five fractions; 118 g of orange oil was recovered after concentration, which was a mixture of the pivaloyloxy enol ether and the phenolic enol ether (Rf values are 0.62 and 0.22, respectively, in 10% EtOAc-hexanes) along with impurities. The oily pivaloyloxy enol ether was isolated by further chromatography to provide an analytical sample, characterized by IR and ¹HNMR (see Tables 6 and 10).

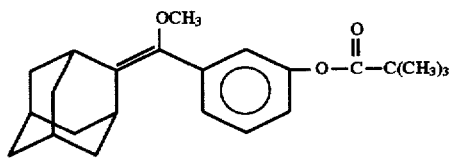

De-acylation of the mixture was completed in 2.5 hours by refluxing the mixture of crude products, 16.5 g of K₂CO₃ and 300 ml of MeOH. After removal of solvents on a rotavap, an orange muddy solid was obtained. The solid was treated with 200 ml of H₂O and then scatched vigorously with a spatula to afford a filterable material. The solid was filtered and washed thoroughly with 1.5 L of H₂O. After removal of most of the moisture under vacuum, the slightly yellow solid was redissolved in 600 ml of CH₂Cl₂ (with gentle heating if necessary) and dried over Na₂SO₄. The solution was filtered on a Buchner funnel, packed with 40 g of silica gel. Upon concentration to the half volume, a white solid began to fall out of the solution. Recrystallization in a mixture of 1:1 CH₂Cl₂ and hexane gave 58.79 g (67%) of white phenol enol ether (mp: 131–133). Another 20–22 g of product could be collected from the mother liquor after chromatography.

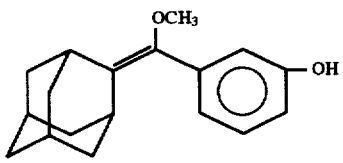

EXAMPLE 8

3-Acetoxybenzaldehyde

3-Hydroxybenzaldehyde (10 g., 81.88 mmol) was dissolved in 150 ml dichloromethane under argon. Triethylamine (17.12 ml, 0.123 mol) and dimethylaminopyridine (5 mg.) were added, and the resulting stirred solution was treated with acetic anhydride (8.5 ml, 90 mmol). After stirring for fifteen hours, the reaction mixture was transferred to a separatory funnel using an additional 50 ml dichloromethane. The organic layer was washed with water (2×100 ml) and concentrated to give a light brown oil weighing 14.85 g. Plug filtration through silica gel using dichloromethane furnished 13.3 g (quant.) of a light orange oil which was shown by NMR and IR to be pure enough for use in subsequent reactions (see Tables 3 and 7).

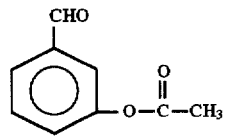

The aldehyde was converted to the corresponding dimethyl acetal by way of the general procedure in Example 4. The oily product, which was homogeneous according to TLC, was obtained in good yield. The structure was confirmed by proton NMR and IR spectra (see Tables 4 and 8). Conversion of the acetal to diethyl 1-methoxy-1-(3-acetoxyphenyl) methane phosphonate was carried out as in Example 5. NMR and IR spectral data confirmed the structure (see Tables 5 and 9) and indicated that the crude product (oil) was pure enough for subsequent use.

EXAMPLE 9

Diethyl-1-methoxy-1-(3-hydroxyphenyl) methanephosphonate

Diethyl-1-methoxy-1-(3-acetoxyphenyl) methanephosphonate from Example 8 (10.29 g., 32.56 mmol) was dissolved in methanol (35 ml). Water (5 ml), and sodium bicarbonate (5 g, 60 mmol) were then added with stirring. After 48 hours at room temperature, the reaction mixture was concentrated in vacuo to remove methanol. The residue was treated with 150 ml dichloromethane and washed with water (2×50 ml). The organic layer was rotory evaporated and pumped at high vacuum to yield 8.21 g. (93%) of the product as a light yellow, viscous oil. Spectral data (Tables 5 and 9) are in accordance with the structure:

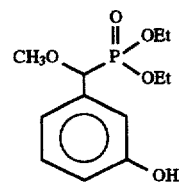

EXAMPLE 10A

6-Methoxynaphthalene-1-carboxaldehyde dimethyl acetal

6-Methoxynaphthalene-1-carbonitrile was synthesized from 6-methoxy-1-tetralone by the method of Harvey, R. G., et al., *J. Org. Chem.*, 48:5134 (1983). The nitrile (354.6 mg., 1.94 mmol) was dissolved in 10 ml dry toluene under argon. The solution was cooled to −78° in a dry ice/acetone bath. A toluene solution of DIBAL (1.3 ml of a 1.5M solution, 1.95 mmol) was added dropwise by syringe with stirring. After 10 minutes the mixture was warmed slowly to room temperature and partitioned between 3N HCl and dichloromethane (25 ml of each). The organic layer was washed with two additional portions of 3N HCl. The combined aqueous layers were back-extracted several times with 10 ml portions of dichloromethane. The combined organics were dried over Na$_2$SO$_4$ and concentrated to yield yellow crystals of the aldehyde which were immediately dissolved in methanol (10 ml) and trimethyl orthoformate (0.25 ml, 2.29 mmol). Several crystals of p-toluenesulfonic acid were added, and the solution was stored for 3 days in the refrigerator. A small amount of NaHCO$_3$ was added and the solvents were stripped. The residue was taken up in minimal dichloromethane and chromatographed on a silica gel column using hexanes as the eluant. The appropriate fractions were evaporated to furnish 395 mg. of the title compound (88% yield for 2 steps) as a light yellow oil which was homogeneous on TLC and exhibited no carbonyl absorption in the infrared spectrum. NMR and IR spectral data are consistent with the structural assignment.

IR (CHCl$_3$, cm$^{-1}$): 2995, 2822, 1622, 1598, 1509, 1465, 1430, 1370, 1250, 1109, 1050, 841.

NMR (CDCl$_3$, ppm): 3.36 (6H, s); 3.92 (3H, s); 5.85 (1H, s); 7.16 (1H, d); 7.18 (1H, dd); 7.42 (1H, t); 7.56 (1H, d, J=7.08 Hz); 7.72 (1H, d, J=8.11 Hz); 8.19 (1H, d, J=9.09).

EXAMPLE 10B

Diethyl 1-methoxy-1-(6-methoxynaphth-1-yl) methane phosphonate

The title phosphonate was synthesized according to the general procedure described in Example 5. Spectral data confirm the product structure.

IR (CHCl$_3$, cm$^{-1}$): 2994, 1619, 1594, 1504, 1458, 1429, 1372, 1242 (P=O), 1050 (br), 968, 845, 810.

NMR (CDCl$_3$, ppm): 3.38 (3H, s); 3.92 (3H, s); 3.9–4.06 (4H, m); 5.25 (1H, d, J=16.4 Hz); 7.15 (1H, d, J=2.2 Hz); 7.18 (1H, dd, J=9.3, 2.85 Hz); 7.72 (1H, d, J=8.05 Hz); 8.12 (1H, d, J=9.28 Hz).

EXAMPLE 11A

6-Methoxy-2-naphthaldehyde

6-Methoxy-2-naphthaldehyde was synthesized, using a Bouveault reaction [E. A. Evans, *J. Chem. Soc.*, 4691 (1956); P. T., Izzo, et al., *J. Org. Chem.*, 24:701 (1959); D. C. Owsley, et al., *J. Org. Chem.*, 38:901 (1973)], by lithiating 5.08 g. (21.4 mmol) of 6-methoxy-2-bromonaphthalene (dissolved in 50 ml dry THF) with n-butyllithium (13.7 ml, 21.8 mmol, 1.6M) at −78° and quenching the aryllithium with dropwise addition of sieve-dried dimethylformide (1.8 ml, 23.2 mmol). After allowing the reaction to warm slowly to 0°, the intermediate aryl hydroxytamine was acidified with 3N HCl at 0° C., facilitating amine elimination to the desired aldehyde. The solution was partitioned between EtOAc and 3N HCl, washing the aqueous layer 3 times with EtOAc to recover all the aldehyde, and then the combined EtOAc solutions were washed with saturated NaHCO$_3$ solution and dried over Na$_2$SO$_4$. After decanting and evaporating the solution, the resultant oil was dissolved in minimal CH$_2$Cl$_2$, followed by addition of hexanes until the solution clouded. Refrigeration for 48 hours afforded 2.292 g (73%) of white crystals upon filtration, which melted at 47°–48°.

IR (CHCl$_3$, cm$^{-1}$): 1685 (C=O), 1618, 1475, 1389, 1263, 1190, 1168, 1027, 895, 856, 839.

$^1$H NMR (CDCl$_3$, ppm): 3.94 (3H, s); 7.16 (1H, d, J=2.44 Hz); 7.21 (1H, dd, J=8.88, 2.44 Hz); 7.79 (1H, d, J=8.55 Hz); 7.87 (1H, d, J=8.85 Hz); 7.90 (1H, d, J=8.55 Hz); 7.87 (1H, d, J=8.85 Hz); 7.90 (1H, dd, J=8.54, 1.52 Hz); 8.23 (1H, s); 10.07 (1H, s).

EXAMPLE 11B

6-Methoxy-2-naphthaldehyde dimethyl acetal

The 6-methoxy-2-naphthyldimethyl acetal was synthesized in 61% yield (m.p. 27°) according to the procedure described in Example 4.

IR (CHCl$_3$, cm$^{-1}$): 2930, 2825, 1629, 1604, 1480, 1260, 1190, 1167, 1098, 1046, 890, 850.

$^1$H NMR (CDCl$_3$, ppm): 3.38 (6H, s); 3.93 (3H, s); 5.54 (1H, s); 7.15–7.18 (2H, m); 7.52 (1H, dd, J=8.55, 1.51 Hz); 7.75 (1H, d, J=8.55 Hz); 7.76 (1H, d, J=8.55 Hz); 7.87 (1H, s).

EXAMPLE 11C

Diethyl 1-methoxy-1-(6-methoxynapth-2-yl) methane phosphate

The corresponding phosphonate was synthesized in 60% yield (oil) as described in Example 5.

IR (CHCl$_3$, cm$^-$): 2998, 1619, 1603, 1480, 1390, 1258 (P=O), 1161, 1094, 1050 (br), 970, 852.

$^1$H NMR (CDCl$_3$, ppm): 1.21 (3H, t, J=7.16 Hz); 1.26 (3H, t, J=7.16 Hz); 3.41 (3H, s); 3.92 (3H, s); 4.04–4.11 (4H, m); 4.64 (1H, d, J=15.41 Hz); 7.14–7.17 (2H, m); 7.54 (1H, d, J=8.68 Hz); 7.75 (1H, d, J=8/86 Hz); 7.76 (1H, d, J=8.47 Hz); 7.82 (1H, s).

EXAMPLE 11D

7-Methoxy-2-naphthaldehyde

7-Methoxy-2-naphthaldehyde was synthesized in 48% yield (oil) using the Bouveault reaction as described above.

IR (CHCl$_3$, cm$^{-1}$): 1687 (C=O), 1601, 1460, 1389, 1331, 1266, 1175, 1115, 1030, 842.

$^1$H NMR (CDCl$_3$, ppm): 3.97 (3H, s); 7.28–7.33 (2H, m); 7.80–7.89 (3H, m); 8.25 (1H, s); 10.15 (1H, s).

EXAMPLE 11E

7-Methoxy-2-naphthaldehyde dimethyl acetal

The corresponding dimethyl acetal was synthesized in 86% yield (oil), following the conditions described in Example 4.

$^1$H NMR (CDCl$_3$, ppm): 3.38 (6H,s); 3.93 (3H, s); 5.55 (1H,s); 7.15–7.18 (2H, m); 7.42 (1H, dd, J=8.03, 1.95 Hz); 7.75 (1H, d, J=9.77 Hz); 7.78 (1H, d, J=8.36 Hz); 7.85 (1H, s).

EXAMPLE 11F

Diethyl 1-methoxy-1-(7-methoxynaphth-2-yl) methane phosphonate

Diethyl 1-methoxy-1-(7-methoxynaphth-2-yl)methane phosphonate was synthesized in 65% yield (oil) following the general procedure outlined in Example 5.

IR (CHCl$_3$, cm$^{-1}$): 2295, 1630, 1603, 1460, 1390, 1256 (P=O ), 1092, 1050 (br), 1027 (br), 970, 908, 840.

$^1$HNMR (CDCl$_3$, ppm): 1.22 (3H, t, J=7 Hz); 1.27 (3H, t, J=7 Hz); 3.43 (3H, s); 3.93 (3H, s); 4.04–4.11 (4H, m); 4.66 (1H, d, J=15.6 Hz); 7.15–7.17 (2H, m); 7.43 (1H, d, J=7.93 Hz); 7.73 (1H, d); 7.78 (1H, d, J=8.46 Hz); 7.82 (1H, s).

TABLE 2

| | Acetal (A) | Phosphonate (B) | Enol Ether (C) |
|---|---|---|---|
| | $X^1$-(3-Ar-1)-C(OR^3)(OR^3)H with $R^2$ | $X^1$-(3-Ar-1)-C(OR^3)(PO(OEt)_2)H with $R^2$ | $X^1$-(3-Ar-1)-C(OR^3)=AD with $R^2$ |

| Example | $R^2$, $R^3$, $X^1$ | | Yield % (Melting Point) | |
|---|---|---|---|---|
| 12 | OCH_3, Et, H | 100 | 99 | 90 |
| 13 | Br, CH_3, H | 91 | 89 | 86 (99–101) |
| 14 | NO_2, CH_3, H | 100 | 93 | |
| 15 | OCOC(CH_3)_3 CH_3, H | 85 | 83 | 66 + 14% of 17C |
| 16 | OAc, CH_3, H | 97 | 94 | 79% of 17C (131–133) |
| 17 | OH, CH_3, H | Poor | Poor | |
| 18 | OCH_3, CH_3, H | 99 | 94 | 93–95 (34–37) |
| 19 | OCH_3, —CH_2CH_2—, H | 98 | $R^3$ = —EtOEt 64 | $R^3$ = —EtOEt 61 |
| 20 | OCH_3, CH_2C_6H_5, H | 72 | 41 | 98 |
| 21 | OCH_3, CH_3, 4-OEt | 99 (65–67) | 95 | 95 (79–81) |
| 22 | OCH_3, CH_3, 2-CH_3 | 93 | 84 | 64 (84–86) |
| 23 | H, CH_3, 4-OCH_3 | 99 | 83 | 88 (77–78.5) |

Enol ether yields based on 2-Adamantanone

TABLE 3

$^1$HNMR SPECTRA OF ALDEHYDES
[All spectra (Tables 3–6) were obtained at 400MHz in CDCl_3.
Chemical Shifts (δ) are expressed in p.p.m. relative to tetramethyl silane]

$X^1$-(3-Ar-1)-CHO with $R^2$

| Example | $R^2$ | | $X^1$ | Aryl | Ar C$\underline{H}$O |
|---|---|---|---|---|---|
| 24 | $R^2$ = —OCOC(CH_3)_3 $X^1$ = —H | 1.36(9H, s, t-butyl) | — | 7.28–7.99(4H, m) | 9.99(1H, s) |
| 25 | $R^2$ = —OCOCH_3 $X^1$ = —H | 2.36(3H, s, OAc) | — | 7.36–7.85(4H, m) | 10.02(1H, s) |
| 26 | $R^2$ = OCH_3 $X^1$ = 2-CH_3 | 3.85(3H, s) | 2.52(3H, s) | 7.06(1H, d, 7.9Hz) 7.29(1H, dd, 7.9, 7.7Hz) 7.41(1H, d, 7.7Hz) | 10.31(1H, s) |
| 27 | $R^2$ = OCH_3 $X^1$ = 4-OCH_2CH_3 | 3.94(3H, s) | 1.52(3H, t, 7Hz) 4.20(2H, q, 7Hz) | 6.97(1H, d, 8.2Hz) 7.41(1H, d, 1.8Hz) 7.44(1H, dd, 8.2, 1.8Hz) | 9.85(1H, s) |
| 28 | $R^2$ = OCH_3 $X^1$ = -5-CHO | 3.93(3H, s) | 10.08(1H, s) | 7.65(2H, s) 7.96(1H, s) | 10.08(1H, s) |

TABLE 4

1HNMR SPECTRA OF ACETALS

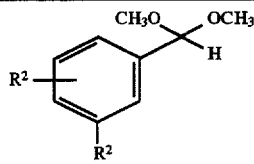

| Example | R² | —C<u>H</u>(OCH₃)₂ | —CH(OC<u>H</u>₃)₂ | Aryl | R² |
|---|---|---|---|---|---|
| 29 | m-OCH₃ | 5.35(1H, s) | 3.33(6H, s) | 6.87(1H, br d, 8.1Hz)<br>7.0–7.03(2H, m)<br>7.27(1H, t, 8.1Hz) | 3.81(3H, s, AROCH₃) |
| 30 | p-OCH₃ | 5.34(1H, s) | 3.30(6H, s) | 6.88(2H, d, 8.5Hz)<br>7.35(2H, d, 8.8Hz) | 3.80(3H, s, ArOCH₃) |
| 31 | m-Br | 5.39(1H, s) | 3.34(6H, s) | 7.26(1H, m)<br>7.40(1H, d, 7.8Hz)<br>7.48(1H, d, 7.8Hz)<br>7.64(1H, d, 1.5Hz) | — |
| 32 | m-NO₂ | 5.49(1H, s) | 3.36(6H, s) | 7.57(1H, m)<br>7.80(1H, d, 7.7Hz)<br>8.21(1H, br d, 8Hz)<br>8.35(1H, s) | — |
| 33 | m-O—C(=O)—C(CH₃)₃ | 5.40(1H, s) | 3.31(6H, s) | 7.01(1H, br d, 7.9Hz)<br>7.15(1H, d, 1.8Hz)<br>7.28(1H, d, 7.6Hz)<br>7.36(1H, dd, 7.7, 7.9Hz) | 1.34(9H, s, t-butyl) |
| 34 | m-OAc | 5.42(1H, s) | 3.32(6H, s) | 7.06(1H, m)<br>7.20(1H, s)<br>7.32(1H, d, 7.6Hz)<br>7.38(1H, dd, 8, 7.6Hz) | 2.30(3H, s, OAc) |
| 35 | m-OH | 5.36(1H, s) | 3.34(6H, s) | 6.81(1H, d, 8Hz)<br>6.96(1H, brs)<br>7.01(1H, d, 7.6Hz)<br>7.24(1H, m) | — |

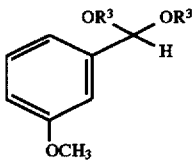

| Example | R³ | ArC<u>H</u>(OR³)₂ | ArOC<u>H</u>₃ | Aryl | R³ |
|---|---|---|---|---|---|
| 36 | —CH₂CH₃ | 5.40(1H, s) | 3.75(3H, s) | 6.78(1H, m)<br>6.97–7.0(2H, m)<br>7.20(1H, m) | 1.18(6H, t, 7Hz)<br>3.26–3.59(4H, m) |
| 37 | —CH₂CH₂— | 5.80(1H, s) | 3.82(3H, s) | 6.90(1H, m)<br>7.02(1H, d, 1.4Hz)<br>7.06(1H, d, 7.8Hz)<br>7.29(1H, dd, 8, 7.8Hz) | 4.0–4.15(4H, m) |
| 38 | —CH₂C₆H₅ | 5.68(1H, s) | 3.76(3H, s) | 6.84(1H, br d, 8Hz)<br>7.08–7.20(2H, m)<br>7.25(1H, m) | 4.55(4H, s, —OC<u>H</u>₂Ph)<br>7.28–7.31(10H, m, phenyl) |

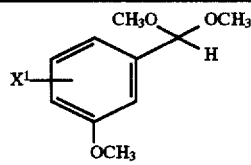

| Example | X² | —C<u>H</u>(OCH₃)₂ | —CH(OC<u>H</u>₃)₂ | ArOC<u>H</u>₃ | Aryl | X² |
|---|---|---|---|---|---|---|
| 39 | -2-CH₃ | 5.45(1H, s) | 3.31(6H, s) | 3.81(3H, s) | 6.81–6.84(1H, m)<br>7.16–7.22(2H, m) | 2.22(3H, s) |
| 40 | 4-OCH₂CH₃ | 5.33(1H, s) | 3.34(6H, s) | 3.90(3H, s) | 6.86(1H, d, 8.2Hz)<br>6.95–7.0(2H, m) | 1.47(3H, t, 7Hz)<br>4.11(2H, q, 7Hz) |
| 41 | 5-CH(OCH₃)₂ | 5.36(1H, s) | 3.33(6H, s) | 3.83(3H, s) | 6.98(2H, s)<br>7.12(1H, s) | 3.33(6H, s)<br>5.36(1H, s) |

TABLE 5

¹HNMR SPECTRA OF PHOSPHONATES $$\text{CH}_3\text{O} \underset{\substack{|\\ \text{H}}}{\overset{\text{PO(OEt)}_2}{\text{C}}} - \text{C}_6\text{H}_4 - \text{R}^2$$

| Example | R² | —CH(OCH₃)P(OEt)₂ (O=) | —CH(OCH₃)P(OEt)₂ (O=) | —CH(OCH₃)P(OCH₂CH₃)₂ (O=) | —CH(OCH₃)P(OCH₂CH₃)₂ (O=) | Aryl | R² |
|---|---|---|---|---|---|---|---|
| 42 | m-OCH₃ | 4.46(1H, d, 15.6Hz) | 3.37(3H, s) | 1.21 and 1.25 (6H, two t. 7Hz) (4H, m) | 3.90–4.10 7.00(2H, m) | 6.85(1H, m) (3H, s, ArOCH₃) 7.26(1h, m) | 3.80 |
| 43 | p-OCH₃ | 4.45(1H, d, 14.9Hz) | 3.35(3H, s) | 1.18–1.29 (6H, m) | 3.89–4.12 (4H, m) | 6.91(2H, d, 8.8Hz) 7.36(2H, dd, 8.72Hz) | 3.81 (3H, s, ArOCH₃) |
| 44 | m-Br | 4.51(1H, d, 15.8Hz) | 3.44(3H, s) | 1.30 and 1.31 (6H, two t, 7Hz) | 4.03–4.18 (4H, m) | 7.29(1H, m) 7.42(1H, d, 7.1Hz) 7.49(1H, br d, 8Hz) 7.62(1H, br s) | — |
| 45 | m-NO₂ | 4.61(1H, d, 15.9Hz) | 3.46(3H, s) (6H, m) | 1.24–1.36 (4H, m) | 4.05–4.19 7.80(1H, d, 7.6Hz) 8.20(1H, br d, 8.1Hz) 8.30(1H, d, 1.7Hz) | 7.57(1H, m) | — |
| 46 | m-O—C—C(CH₃)₃ (‖O) | 4.49(1H, d, 15.8Hz) | 3.38(3H, s) | 1.16–1.31 (6H, m) | 3.92–4.11 (4H, m) | 7.01(1H, br d, 7.9Hz) 7.13(1H, d, 1.8Hz) 7.27(1H, d, 7.7Hz) 7.35(1H, t, 7.9Hz) | 1.33 (9H, s, t-butyl) |
| 47 | m-OAc | 4.51(1H, d, 15.9Hz) | 3.38(3H, s) | 1.19–1.27 (6H, m) | 3.94–4.11 (4H, m) | 7.04(1H, d, 7.8Hz) 7.16(1H, d, 1.4Hz) 7.28(1H, d, 7.6Hz) 7.36(1H, t, 7.8Hz) | 2.27 (3H, s, OAc) |
| 48 | m-OH | 4.48(1H, d, 15.6Hz) | 3.38(3H, s) | 1.22 and 1.28 (6H, two t, 7Hz) | 3.85–4.14 (4H, m) | 6.81(1H, d, 8.1Hz) 6.87(1H, d, 7.3Hz) 7.15(1H, d, 1.6Hz) 7.20(1H, t, 7.8Hz) | — |

TABLE 5-continued

¹HNMR SPECTRA OF PHOSPHONATES $$\text{R}^3\text{O}\diagdown\underset{\text{H}}{\overset{\text{PO(OEt)}_2}{\diagup}}\text{—Ar, Ar = 3-methoxyphenyl (OCH}_3\text{)}$$

| Example | R³ | $-\underline{\text{CH}}(\text{OR}^3)\overset{\text{O}}{\overset{\|}{\text{P}}}(\text{OEt})_2$ | ArO<u>CH</u>₃ | $-\text{CH}(\text{O}\underline{\text{R}^3})\overset{\text{O}}{\overset{\|}{\text{P}}}(\text{OC}\underline{\text{H}}_2\text{CH}_3)_2$ | $-\text{CH}(\text{OR}^3)\overset{\text{O}}{\overset{\|}{\text{P}}}(\text{OCH}_2\underline{\text{CH}}_3)_2$ | Aryl | R³ |
|---|---|---|---|---|---|---|---|
| 49 | —CH₂CH₃ | 4.57(1H, d, 16.1Hz) | 3.73(3H, s) | 1.12–1.24 (6H, m) | 3.90–4.15 (4H, m) | 6.77(1H, m) 6.91–6.94(2H, m) 7.15–7.22(1H, m) | 1.12–1.24(3H, m) 3.40–3.58(2H, m) |
| 50 | —CH₂CH₃<br>\|<br>OCH₂CH₃ | 4.73(1H, d, 15.7Hz) | 3.81(3H, s) | 1.17–1.29 (6H, m) | 3.95–4.76 (4H, m) | 6.85(1H, m) 6.99–7.02(2H, m) 7.26(1H, m) | 1.17–1.29(3H, m) 3.51(2H, q, 7Hz) 3.56–3.79(4H, m) |
| 51 | —CH₂C₆H₅ | 4.66(1H, d, 16.1Hz) | 3.83(3H, s) | 1.21 and 1.26 (6H, two t, 7.1Hz) | 3.88–4.12 (4H, m) | 6.90(1H, m) 7.02–7.06(2H, m) 7.27–7.31(1H, m) | 4.41 and 4.72 (2H, two d, 12Hz) 7.29–7.40(5H, m, phenyl) |

TABLE 5-continued

¹HNMR SPECTRA OF PHOSPHONATES

Structure: CH₃O-CH(PO(OEt)₂)-Aryl(X¹)(OCH₃ at 3-position)

| Example | X² | —C<u>H</u>(OCH₃)P(OEt)₂ ‖O | —CH(OC<u>H</u>₃)P(OEt)₂ ‖O | ArOC<u>H</u>₃ | —CH(OCH₃)P(OC<u>H</u>₂CH₃)₂ ‖O | —CH(OCH₃)P(OCH₂C<u>H</u>₃)₂ ‖O | Aryl | X² |
|---|---|---|---|---|---|---|---|---|
| 52 | 2-CH₃ | 4.84(1H, d, 15.6Hz) | 3.33(3H, s) | 3.82(3H, s) | 3.86-4.11 (4H, m) | 1.21 and 1.27 (6H, two t, 7.1Hz) | 6.81(1H, d, 7.3Hz) 7.16-7.23(2H, m) | 2.24(3H, s) |
| 53 | 4-OCH₂CH₃ | 4.41(1H, d, 15Hz) | 3.34(3H, s) | 3.87(3H, s) | 3.84-4.11 (4H, m) | 1.19 and 1.26 (6H, two t, 7.1Hz) | 6.83(1H, d, 8.2Hz) 6.91(1H, dd, 6.1, 2.1Hz) 7.0(1H, s) | 1.44(3H, t, 7Hz) 4.04-4.11 (2H, q, 7Hz) |
| 54 | 5-CHO | 4.53(1H, d, 15.9Hz) | 3.40(3H, s) | 3.85(3H, s) | 4.01-4.14 (4H, m) | 1.20-1.33 (6H, m) | 7.25(1H, s) 7.34(1H, s) 7.51(1H, s) | 9.95(1H, s) |
| 55 | 5-CH(OCH₃)P(OEt)₂ ‖O | 4.46(1H, d, 15.9Hz) | 3.36(3H, s) | 3.80(3H, s) | 3.91-4.10 (4H, m) | 1.18-1.27 (6H, m) | 6.97(2H, s) 7.05(1H, s) | 3.36(3H, s) 4.47(1H, d, 15.9Hz) 1.18-1.27(6H, m) 3.91-4.10(4H, m) |

TABLE 6

¹HNMR SPECTRA OF ENOL ETHERS

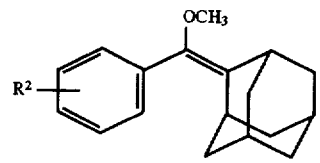

| Example | R² | OCH₃<br>Ar—C=Ad | Adamantyl Protons | Hα₂(Ad) | Hα₂(Ad) | Aryl | R² |
|---|---|---|---|---|---|---|---|
| 56 | m-OCH₃ | 3.31(3H, s) | 1.75–2.05(12H, m) | 2.66(1H, br s) | 3.27(1H, br s) | 6.82–6.94(3H, m)<br>7.23–7.30(1H, m) | 3.83<br>(3H, s, OCH₃) |
| 57 | p-OCH₃ | 3.27(3H, s) | 1.72–1.97(12H, m) | 2.59(1H, br s) | 3.23(1H, br s) | 6.88(2H, d, 8.8Hz)<br>7.23(2H, d, 8.8Hz) | 3.81<br>(3H, s, OCH₃) |
| 58 | m-Br | 3.30(3H, s) | 1.74–2.02(12H, m) | 2.60(1H, br s) | 3.24(1H, br s) | 7.18–7.27(2H, m)<br>7.41(1H, dd, 7.2, 2.1Hz)<br>7.47(1H, br, s) | — |
| 59 | m-OCC(CH₃)₃<br>‖<br>O | 3.30(3H, s) | 1.73–1.99(12H, m) | 2.65(1H, br s) | 3.25(1H, br s) | 6.95–7.03(2H, m)<br>7.16(1H, d, 7.6Hz)<br>7.34(1H, dd, 8.7, 6Hz) | 1.36<br>(9H, s, t-butyl) |

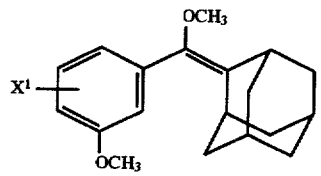

| Example | X² | OCH₃<br>Ar—C=Ad | ArOCH₃ | Adamantyl Protons | Hα₂(Ad) | Hα₂(Ad) | Aryl | X² |
|---|---|---|---|---|---|---|---|---|
| 60 | 2-CH₃ | 3.23(3H, s) | 3.85(3H, s) | 1.65–1.94(12H, m) | 2.12(1H, br s) | 3.27(1H, br s) | 6.79(1H, d, 7.6Hz)<br>6.82(1H, d, 8.2Hz)<br>7.13(1H, dd, 8.2, 7.6Hz) | 2.19(3H, s) |
| 61 | 4-OCH₂CH₃ | 3.28(3H, s) | 3.85(3H, s) | 1.73–1.96(12H, m) | 2.63(1H, br s) | 3.22(1H, br s) | 6.80–6.85<br>(3H, m) | 1.46(3H, t, 7Hz)<br>4.10(2H, q, 7Hz) |

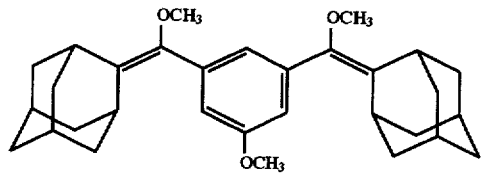

| Example | X² | OCH₃<br>Ar—C=Ad | ArOCH₃ | Adamantyl Protons | Hα₂(Ad) | Hα₂(Ad) | Aryl | X¹ |
|---|---|---|---|---|---|---|---|---|
| 62 | H | 3.30(6H, s) | 3.80(3H, s) | 1.78–1.96(24H, m) | 2.64(2H, br s) | 3.23(2H, br s) | 6.80–6.82(3H, m) | — |

TABLE 6-continued

¹HNMR SPECTRA OF ENOL ETHERS

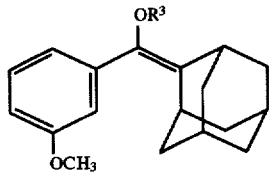

| Example | $R^3$ | $Ar-\underset{OCH_3}{\underset{|}{C}}=Ad$ | $ArOC\underline{H_3}$ | Adamantyl Protons | $H\alpha_2(Ad)$ | $H\alpha_2(Ad)$ | Aryl | $R^3$ |
|---|---|---|---|---|---|---|---|---|
| 63 | —CH₂CH₃ | — | 3.80(3H, s) | 1.76–1.98(12H, m) | 2.67(1H, br s) | 3.26(1H, br s) | 6.81(1H, m) 6.87–6.92(2H, m) 7.24(1H, m) | 1.14(3H, t, 7Hz) 3.47(2H, q, 7Hz) |
| 64 | —CH₂CH₃ \| OCH₂CH₃ | — | 3.81(3H, s) | 1.77–1.98(12H, m) | 2.68(1H, br s) | 3.33(1H, br s) | 6.82(1H, m) 6.89–6.92(2H, m) 7.24(1H, m) | 1.20(3H, q, 7Hz) 3.48(2H, q, 7Hz) 3.50–3.59 (4H, m) |
| 65 | —CH₂C₆H₅ | — | 3.87(3H, s) | 1.63–2.22(12H, m) | 2.71(1H, br s) | 3.22(1H, br s) | 6.89–7.01(3H, m) 7.10–7.27(1H, m) | 4.49(2H, s) 7.11–7.57 (5H, m) |

TABLE 7

IR SPECTRA OF ALDEHYDES
(All IR Spectra (Tables 7–10) Are Neat Unless Otherwise Indicated, cm⁻¹)

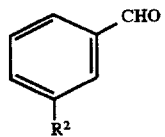

| Example | $R^2$ | |
|---|---|---|
| 66 | m-OCC(CH₃)₃ (O=) | 2964, 1745 (ester C=O), 1690 (aldehyde C=O), 1598, 1582, 1475, 1234, 1132, 1105 |
| 67 | m-OAc | 2836, 1760 (ester C=O), 1695 (aldehyde C=O), 1598, 1583, 1376, 1195 |

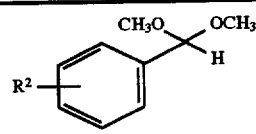

| | $X^1$ | |
|---|---|---|
| 68 | 4-OCH₂CH₃ (CHCl₃) | 2980, 2825, 2744, 2720, 1675 (C=O), 1580, 1572, 1460, 1262, 1130, 1027, 800 |
| 69 | 5-CHO (CHCl₃) | 3005, 2837, 2723, 1695 (C=O), 1590, 1462, 1295, 1055, 862 |
| 70 | 2-CH₃ | 2995, 2930, 2830, 2720, 1685 (C=O) 1590, 1580, 1465, 1257, 1093, 1010, 780 |

TABLE 7-continued

IR SPECTRA OF ALDEHYDES
(All IR Spectra (Tables 7–10) Are Neat Unless Otherwise Indicated, cm⁻¹)

| 71 | 5-CH(OCH₃)P(OEt)₂ (O=) | 2976, 2925, 2820, 2722, 1690 (C=O) 1590, 1460, 1247 (P=O), 1155, 1040, 865 |
|---|---|---|

TABLE 8

IR SPECTRA OF ACETALS

| Example | $R^2$ | |
|---|---|---|
| 72 | m-NO₂ | 3080, 2930, 2825, 1610, 1580, 1525, (ArNO₂), 1345 (ArNO₂), 1205, 1105, 1055, 982, 805, 738, 715 |
| 73 | m-OCC(CH₃)₃ (O=) | 2980, 2824, 1748, (ester C=O), 1606, 1588, 1478, 1235, 1145, 1110, 1055, 770 |
| 74 | m-OAc | 2930, 2824, 1760 (ester C=O), 1605, 1585, 1365, 1200, 1098, 1050 |
| 75 | m-OH | 3450(OH), 2932, 2824, 1598, 1586, 1450, 1348, 1190, 1098, 1050, 778 |
| 76 | p-OMe | 2942, 2930, 2820, 1606, 1580, 1508, 1245, 1168, 1096, 1050, 820 |

TABLE 8-continued

IR SPECTRA OF ACETALS

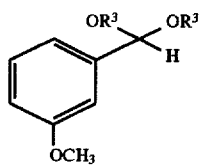

| Example | $R^3$ | |
|---|---|---|
| 77 | $-CH_2CH_3$ | 2985, 2940–50, 2870, 1600, 1585, 1485, 1330, 1260, 1100, 1030–50, 890, 875, 695 |
| 78 | $-CH_2CH=_2$ | 2880, 2940–50, 1600, 1585, 1485, 1390, 1315, 1260, 1100, 1030–50, 965, 945, 695 |
| 79 | $-CH_2C_6H_5$ | 3080, 3060, 3020, 2940–50, 1600, 1585, 1485, 1430, 1260, 1100, 1030–50, 865, 695 |

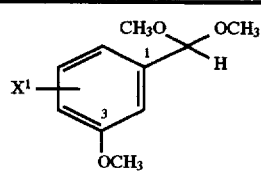

| Example | $X^2$ | |
|---|---|---|
| 80 | 4-OCH$_2$CH$_3$ (CHCl$_3$) | 2995, 2930, 2820, 1604, 1587, 1507, 1410, 1255, 1157, 1133, 1096, 1043, 975, 860 |
| 81 | 5-CH(OMe)$_2$ | 2980, 2940, 2820, 1597, 1460, 1285, 1190 1155, 1055 (br), 985, 855, 790 |
| 82 | 2-CH$_3$ | 2980, 2925, 2820, 1580, 1465, 1350, 1255, 1190, 1075, 1050, 975, 915, 787, 764 |

TABLE 9

IR SPECTRA OF PHOSPHONATES

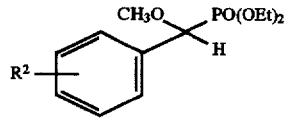

| Example | $R^2$ | |
|---|---|---|
| 83 | m-NO$_2$ | 2950, 1610, 1578, 1526, (ArNO$_2$), 1350 (ArNO$_2$), 1250 (P=O), 1095, 1048, 1022, 970 |
| 84 | m-OCC(CH$_3$)$_3$ (with C=O) | 2970, 1745 (ester C=O), 1603, 1584, 1475, 1272, 1253 (P=O), 1135, 1110, 1050, 1020, 960 |
| 85 | m-OAc | 2974, 1758 (ester C=O), 1603, 1584, 1250 (P=O), 1200, 1095, 1048, 1020 |
| 86 | m-OH | 3220, 3190 (OH), 2890, 1598, 1585, 1452, 1235 (P=O), 1095, 1050, 1020, 965 |
| 87 | p-OMe | 2970, 1603, 1578, 1505, 1250 (P=O), 1090, 1050, 1025, 975 |
| 88 | m-Br | 2975, 1588, 1568, 1470, 1252 (P=O), 1098, 1050, 1024, 968 |
| 89 | m-OMe | 2974, 1596, 1582, 1480, 1255 (P=O), 1098, 1050, 1020, 965 |

TABLE 9-continued

IR SPECTRA OF PHOSPHONATES

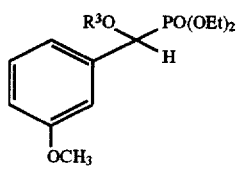

| Example | $R^3$ | |
|---|---|---|
| 90 | $-CH_2CH_3$ | 2975, 2925, 2900, 1595, 1580, 1485, 1435, 1365, 1315, 1255, (P=O), 1100, 1040 (br), 965, 870, 695 |
| 91 | $-CH_3CH_3-O$ $\vert$ Et | 2975, 2925, 2900, 1595, 1580, 1485, 1435, 1365, 1315, 1255 (P=O), 1100, 1040 (br), 965, 790, 695 |
| 92 | $-CH_2C_6H_5$ | 2975, 2925, 2900, 1595, 1580, 1485, 1435, 1365, 1315, 1255 (P=O), 1160, 1100, 1040 (br), 965, 790, 740, 695 |

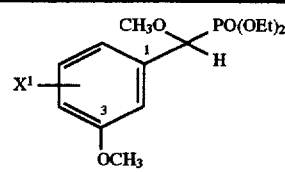

| Example | $X^2$ | |
|---|---|---|
| 93 | 4-OCH$_2$CH$_3$ | 2970, 2922, 2815, 1598, 1585, 1509, 1413, 1387, 1255 (P=O), 1090, 1040 (br), 960, 870, 790, 750 |
| 94 | 5-CH(OCH$_3$)P(OEt)$_2$ (with C=O) | 2978, 2925, 2900, 2820, 1590, 1458, 1387, 1330, 1250 (P=O), 1160, 1100, 1040–50 (br), 960, 870, 785, 695 |
| 95 | 2-CH$_3$ | 2978, 2925, 2900, 2823, 1580, 1465, 1328, 1255 (P=O), 1168, 1050, 1020, 967, 785, 752, 730 |

TABLE 10

IR SPECTRA OF ENOL ETHERS

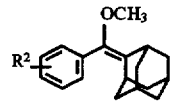

| Example | $R^2$ | |
|---|---|---|
| 96 | m-OCC(CH$_3$)$_3$ (with C=O) | 2900, 2838, 2658, 2640, 2624, 1748 (ester C=O), 1655, 1600, 1575, 1475, 1270, 1110 |
| 97 | p-OMe (CHCl$_3$) | 2905, 2840, 2656, 2640, 2620, 1652, 1602, 1520, 1504, 1240, 1086, 1075, 848 |
| 98 | m-Br (CHCl$_3$) | 2910, 2840, 2655, 2640, 2625, 1650, 1587, 1555, 1465, 1445, 1268, 1095, 1080 |
| 99 | m-OMe | 2900, 2838, 2655, 2640, 2620, 1655, 1600, 1592, 1580, 1574, 1444, 1282, 1240, 1202, 1095, 1078 |

TABLE 10-continued

IR SPECTRA OF ENOL ETHERS

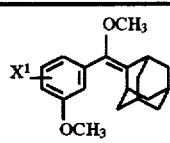

| R³ | |
|---|---|
| 100 | —CH₂CH₃ | 2900, 2840, 2660, 2642, 2625, 1655, 1600, 1590, 1580, 1572, 1480, 1460, 1442, 1425, 1385, 1280, 1240, 1195, 1175, 1045, 890, 782 |
| 101 | CH₂CH₂<br>\|<br>OEt | 2900, 2840, 2660, 2642, 2625, 1655, 1600, 1590, 1580, 1572, 1480, 1460, 1441, 1425, 1380, 1280, 1240, 1195, 1120, 1045, 890, 782 |
| 102 | CH₂C₆H₅ | 2900, 2840, 2660, 2642, 2625, 1655, 1600, 1590, 1580, 1573, 1480, 1425, 1280, 1240, 1195, 1045, 1025, 960, 905, 865, 782, 695 |

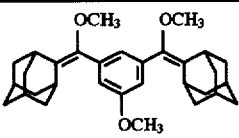

| Example | X¹ | |
|---|---|---|
| 103 | 4-OCH₂CH₃<br>(CHCl₃) | 2900, 2840, 2655, 2640, 2620, 1653, 1598, 1577, 1505, 1460, 1442, 1245, 1135, 1033, 915, 865, 820 |
| 104 | 2-CH₃<br>(CHCl₃) | 2910, 2840, 2660, 2640, 2625, 1575, 1465, 1305, 1253, 1125, 1080, 1030, 970, 955 |

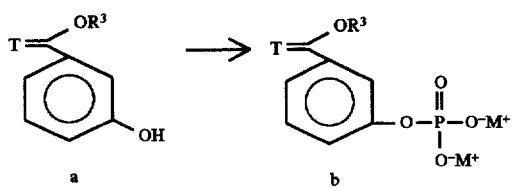

| 105 | H<br>(CHCl₃) | 2910, 2840, 2660, 2642, 2624, 1660, 1590, 1578, 1460, 1440, 1338, 1325, 1245, 1160, 1095, 1078, 840 |

EXAMPLE 106

Phosphorylation of Enol Ether Phenol

The enol ether phenol a (R³=methyl, T=adamant-2-ylidene, from Example 7) was reacted with 2-chloro-2-oxo-1,3,2-dioxaphospholane according to Thuong, N. T., et al., *Bull. Soc. Chim. France*, 2083 (1975) to give a cyclic phosphate triester, which underwent ring opening with NaCN to yield the 2-cyanoethyl diester salt. Ammonium hydroxide then induced a facile β-elimination reaction to a filterable sodium ammonium salt of b (75% yield from a), which was ion exchanged to the disodium salt of b for ¹HNMR (D₂O, 400 MHz); δ1.6–7.9 (12H, m); 2.44 (1H, s); 2.97 (1H, s); 3.22 (3H, s); 6.98 (1H, m, 7.52 Hz); 6.96 (1H, s); 7.05 (1H, m); 7.18 (1H, dd, 7.62, 8.06 Hz). This same salt was obtained directly using sodium methoxide to induce β-elimination.

EXAMPLE 107

Photooxygenation of an Enol Ether Phosphate

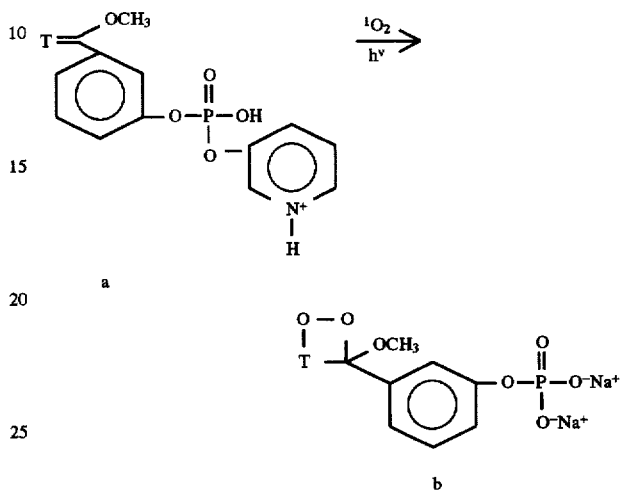

wherein T = adamantane

The sodium ammonium salt a was ion exchanged to the monopyridinium salt. A 0.06M solution of the latter salt was photooxygenated in the presence of O₂ and TPP at 5° C. (Slower reaction rates and increased photolytic damage to the product were experienced with the use of solid phase sensitizers such as Sensitox I or methylene blue on silica gel). Purification on a reversed phase HPLC column at pH 8.6 (Na₂CO₃) and using an acetonitrile-water gradient, followed by lyophilization, provided 3-(2'-spiroadamantane)-4-methoxy-4-(3"-phosphoroyloxy)phenyl-1,2-dioxetane(b) as a faintly yellow solid, in 80% yield.

¹HNMR (D₂O, 400 MHz): 0.85 (1H, d); 1.13 (1H, d); 1.40–1.67 (10H, m); 2.13 (1H, s); 2.75 (1H, s); 3.10 (3H, s); 7.15 (2H, broad, featureless); 7.20 (1H, d, 7.81 Hz); 7.28 (1H, dd, 7.81, 8.09 Hz).

The upfield doublets are characteristic of the beta adamantane ring protons in the dioxetane, which are more shielded by the proximate aromatic ring than in the enol ether. The coalescence of the two aromatic proton resonances into a broad peak at 7.15 ppm mirrors similar behavior in the ¹³C spectrum (D₂O/CD₃OD); two aromatic carbon resonances at 120.95 ppm and 122.10 ppm are broad, low intensity peaks at 0° C., which sharpen and become more intense at 40° C. This indicates restricted rotation of the aromatic substituent, which may introduce a conformational component into the rate of electron transfer decomposition of the anion to the excited state ester.

The above discussion of this invention is directed primarily to preferred embodiments and practices thereof. It will be readily apparent to those skilled in this art that further changes and modifications in the actual implementation of the concepts described herein can easily be made without departing from the spirit and scope of the invention as defined by the following claims.

We claim:

1. A compound having the formula:

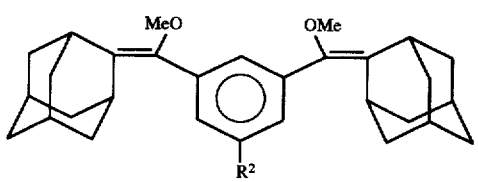

wherein $R^2$ is an ether ($OR^4$) or a thioether ($SR^4$) wherein $R^4$ is a lower alkyl or aralkyl substituent having up to 20 carbon atoms, an acetoxy or pivaloyloxy group, a halogen atom, a nitro group, a hydroxyl group, an amino group, a di(lower alkyl) amino group wherein each lower alkyl substituent contains up to 7 carbon atoms, or an $NHSO_2R^5$ group wherein $R^5$ is tolyl or trifluoromethyl.

2. A compound having the formula:

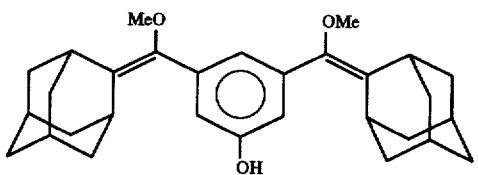

3. A compound having the formula:

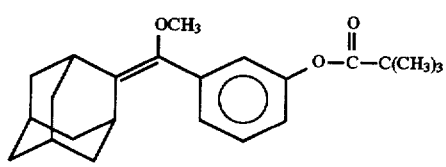

4. A compound having the formula:

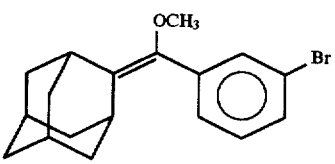

5. A compound having the formula:

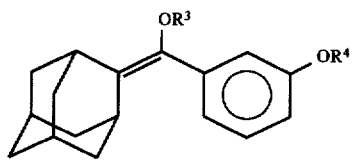

wherein $R^3$ is a substituted or unsubstituted (i) lower alkyl, aralkyl, or heteroaralkyl group having up to 20 carbon atoms, (ii) aryl or heteroaryl group having up to 14 carbon atoms, (iii) alkoxy (lower) alkyl group, (iv) a hydroxy (lower) alkyl group having up to 6 carbon atoms, a (lower) alkyl-$OSiX_3$ group wherein the lower alkyl group contains up to 6 carbon atoms and any X is independently methyl, phenyl, or t-butyl, or (v) amino (lower) alkyl or mono or di(lower) alkylamino alkyl group where each lower alkyl group contains up to 7 carbon atoms; and $R^4$ is a substituted or unsubstituted pivaloyl, allyl, benzyl or o-nitrobenzyl group having up to 20 carbon atoms.

6. A compound in accordance with claim 5 having the formula:

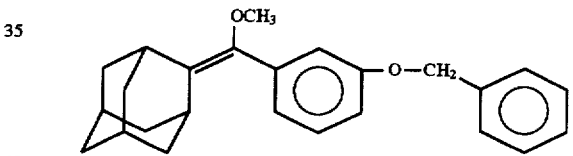

* * * * *